US009760265B2

(12) United States Patent
Yoshigahara et al.

(10) Patent No.: US 9,760,265 B2
(45) Date of Patent: Sep. 12, 2017

(54) INFORMATION PROCESSING DEVICE AND AN INFORMATION PROCESSING METHOD

(71) Applicant: SONY CORPORATION, Tokyo (JP)

(72) Inventors: Takayuki Yoshigahara, Tokyo (JP); Hideki Shimomura, Kanagawa (JP); Seiji Kobayashi, Tokyo (JP); Yoshihiro Wakita, Tokyo (JP)

(73) Assignee: SONY CORPORATION, Tokyo (JP)

( * ) Notice: Subject to any disclaimer, the term of this patent is extended or adjusted under 35 U.S.C. 154(b) by 275 days.

(21) Appl. No.: 14/344,242

(22) PCT Filed: Oct. 25, 2012

(86) PCT No.: PCT/JP2012/006849
§ 371 (c)(1),
(2) Date: Mar. 11, 2014

(87) PCT Pub. No.: WO2013/076917
PCT Pub. Date: May 30, 2013

(65) Prior Publication Data
US 2014/0331157 A1    Nov. 6, 2014

(30) Foreign Application Priority Data

Nov. 25, 2011   (JP) .................................. 2011-257561

(51) Int. Cl.
*G06K 9/00*      (2006.01)
*G06F 3/0484*    (2013.01)
*G06F 19/00*     (2011.01)

(52) U.S. Cl.
CPC ...... *G06F 3/04845* (2013.01); *G06F 3/04842* (2013.01); *G06F 19/327* (2013.01); *G06F 19/3456* (2013.01); *G06F 19/3418* (2013.01)

(58) Field of Classification Search
None
See application file for complete search history.

(56) References Cited

U.S. PATENT DOCUMENTS 7,689,465 B1    3/2010   Shakes et al.
8,073,238 B2 *  12/2011  Nakanishi ............. G06Q 50/22
                                                  382/141
(Continued)

FOREIGN PATENT DOCUMENTS

CN    101328526 A    12/2008
JP    2003-32544 A    1/2003
(Continued)

OTHER PUBLICATIONS

Hartl et al., "Instant medical pill recognition on mobile phones", Robotics and Applications with Symposiz 739: Computational Photography and 740: Computer Vision, Jun. 1-3, 2011.*

(Continued)

*Primary Examiner* — Soo Park
(74) *Attorney, Agent, or Firm* — Oblon, McClelland, Maier & Neustadt, L.L.P.

(57) ABSTRACT

An information processing device, and method use an attribute control unit to change an association between a detected object and an attribute stored in association with the detected object in response to a detected physical action between the detected object and another detected object. By changing an association of an attribute between detected objects allows for an autonomous tracking of substances that are moved between objects.

20 Claims, 32 Drawing Sheets

(56) References Cited

U.S. PATENT DOCUMENTS

| | | | | |
|---|---|---|---|---|
| 8,363,913 | B2* | 1/2013 | Boushey | G06K 9/00 128/921 |
| 8,439,683 | B2* | 5/2013 | Puri | G09B 19/0092 434/127 |
| 8,596,309 | B2* | 12/2013 | Mizuno | A61J 3/002 141/104 |
| 8,606,596 | B1* | 12/2013 | Bochenko | G06Q 10/00 705/2 |
| 8,781,856 | B2* | 7/2014 | Hanina | G06Q 50/22 382/107 |
| 9,129,158 | B1* | 9/2015 | Medasani | G06K 9/00335 |
| 9,155,833 | B2* | 10/2015 | Nelson | A61M 5/168 |
| 2003/0076983 | A1* | 4/2003 | Cox | G06F 19/3475 382/110 |
| 2007/0179359 | A1* | 8/2007 | Goodwin | A63B 71/00 600/300 |
| 2008/0162188 | A1* | 7/2008 | Kripalani | G06Q 50/24 705/3 |
| 2008/0267444 | A1* | 10/2008 | Simons-Nikolova | A61B 5/1123 382/100 |
| 2009/0048871 | A1 | 2/2009 | Skomra | |
| 2010/0042430 | A1* | 2/2010 | Bartfeld | G06F 19/3456 705/2 |
| 2011/0119073 | A1 | 5/2011 | Hanina et al. | |
| 2012/0096405 | A1* | 4/2012 | Seo | G06F 3/04886 715/825 |
| 2012/0179665 | A1* | 7/2012 | Baarman | G06F 19/3475 707/709 |
| 2012/0219176 | A1* | 8/2012 | Guan | G06K 9/00355 382/103 |
| 2012/0251079 | A1* | 10/2012 | Meschter | G06F 19/3406 386/278 |
| 2013/0076898 | A1* | 3/2013 | Philippe | H04N 7/18 348/143 |
| 2013/0157232 | A1* | 6/2013 | Ehrenkranz | G01G 19/4146 434/127 |
| 2013/0203024 | A1* | 8/2013 | Dekar | B25J 11/008 434/127 |
| 2013/0267794 | A1* | 10/2013 | Fernstrom | G01N 33/02 600/301 |
| 2013/0335418 | A1* | 12/2013 | Kim | G06Q 10/00 345/424 |
| 2014/0063242 | A1* | 3/2014 | Hanina | B01D 39/1623 348/143 |
| 2015/0079565 | A1* | 3/2015 | Miller | G09B 23/281 434/252 |

FOREIGN PATENT DOCUMENTS

| | | |
|---|---|---|
| JP | 2005-56213 A | 3/2005 |
| JP | 2005-157877 A | 6/2005 |
| JP | 2006-4421 A | 1/2006 |
| JP | 2008-123365 A | 5/2008 |
| JP | 2009-289067 A | 12/2009 |
| JP | 2011-176599 A | 9/2011 |
| WO | WO 2004/112685 A1 | 12/2004 |

OTHER PUBLICATIONS

Japanese Office Action issued Nov. 24, 2015 in Patent Application No. 2011-257561 (with English Translation).

International Search Report issued Sep. 3, 2013 in PCT/JP2012/006849.

"Statement in accordance with the Notice from the European Patent Office dated Oct. 1, 2007 concerning business methods", Official Journal EPO, XP002456414, Nov. 1, 2007, 1 Page.

"Notice from the European Patent Office dated Oct. 1, 2007 concerning business methods", Official Journal of the European Patent Office, vol. 30, No. 11, XP007905525, Nov. 1, 2007, pp. 592-593.

Combined Chinese Office Action and Search Report issued on May 5, 2016 in Patent Application No. 201280056353.2 (with partial English language translation and English language translation of categories of cited documents).

Office Action issued on Jun. 14, 2016 in Japanese Patent Application No. 2011-257561 (with English language translation).

Office Action dated Mar. 2, 2017 in European Patent Application No. 12788649.7.

Huynh, H.H. et al., "Real time detection, tracking and recognition of medication intake", World Academy of Science, Engineering and Technology 60, Jan. 1, 2009, XP055145789.

Office Action dated Jul. 4, 2017 in Chinese Application No. 201280056353.2, along with an English translation.

\* cited by examiner

Fig. 7
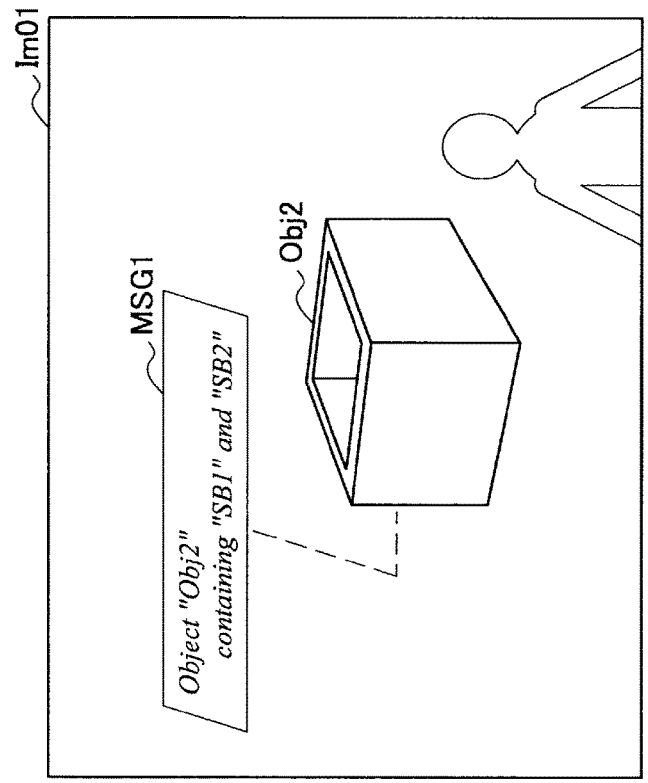
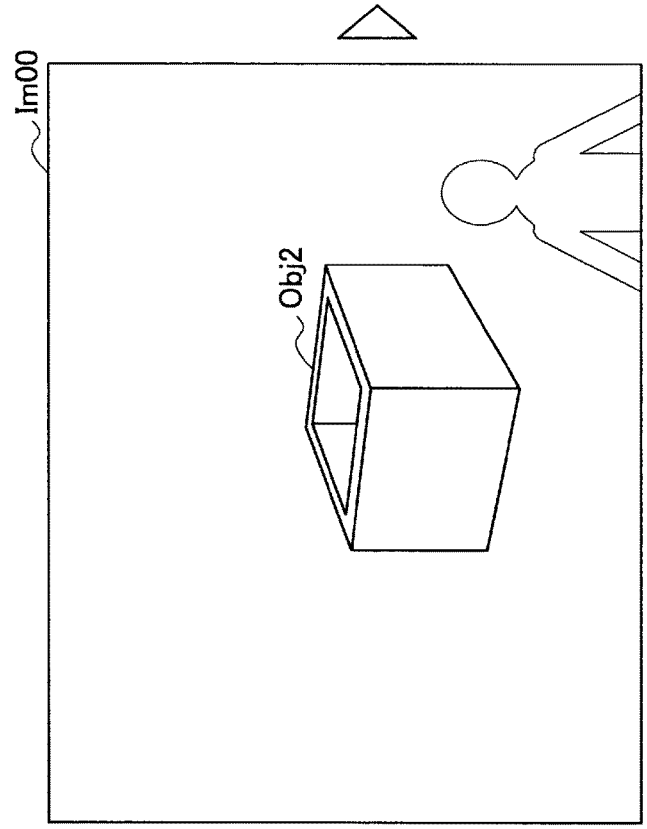

Fig. 8

| OBJECT ID | NAME | PRODUCT NUMBER | TYPE | FEATURE QUANTITY |
|---|---|---|---|---|
| Obj11 | VIAL | VL011 | SOURCE | FD11 |
| Obj12 | SYRINGE | SL012 | TRANSPORTER | FD12 |
| Obj13 | RINGER'S SOLUTION BAG | IV013 | DESTINATION | FD13 |
| .. | .. | .. | .. | .. |

142a

OBJECT DATA

Fig. 9

| TYPE OF SECOND OBJECT (Obj2) | TYPE OF FIRST OBJECT (Obj1) | | |
|---|---|---|---|
| | SOURCE | TRANSPORTER | DESTINATION |
| SOURCE | NO UPDATE | NO UPDATE | |
| TRANSPORTER | Obj1: NO UPDATE<br>Obj2: ADD ATTRIBUTES OF Obj1 | NO UPDATE | |
| DESTINATION | NO UPDATE | Obj1: ELIMINATE<br>Obj2: ADD ATTRIBUTES OF Obj1 | NO UPDATE |

ATTRIBUTE CONTROL TABLE 144a

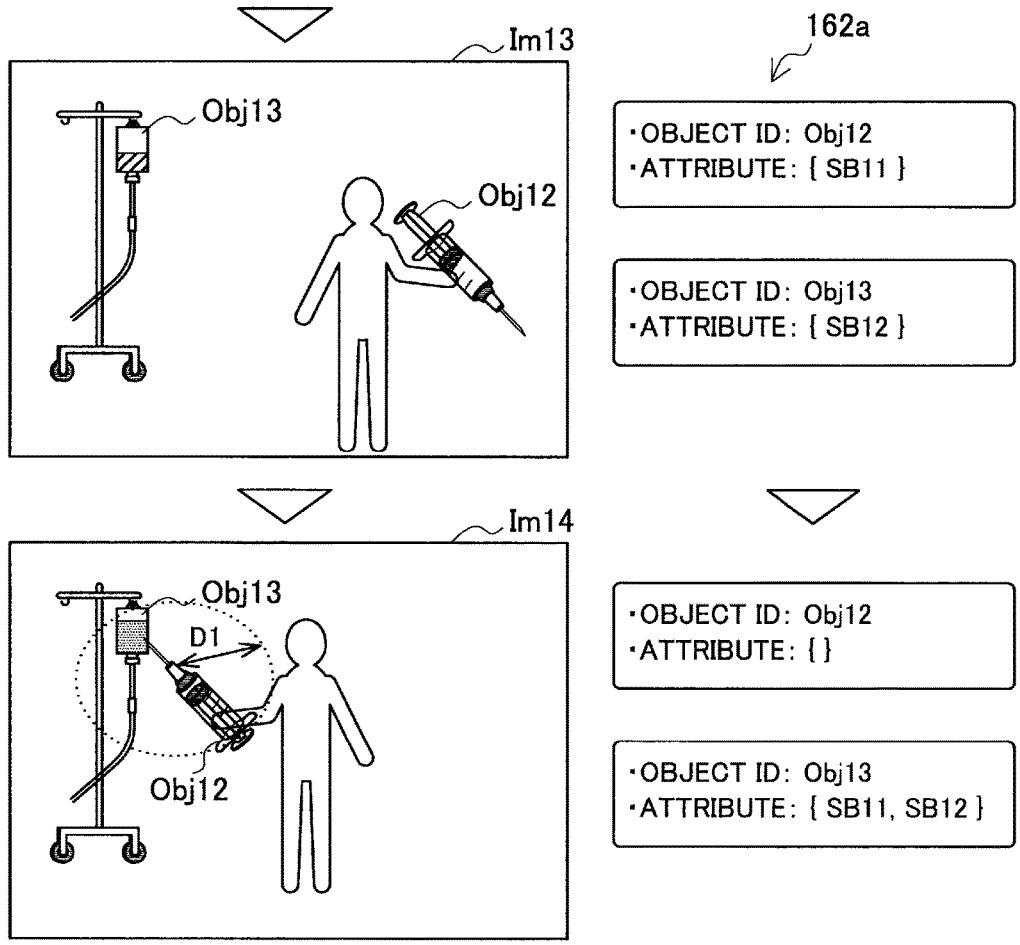

Fig. 15

| OBJECT ID | NAME | PRODUCT NUMBER | TYPE | FEATURE QUANTITY |
|---|---|---|---|---|
| Obj21 | MEDICINE BOTTLE | MB021 | SOURCE | FD21 |
| Obj22 | SPOON | SP022 | TRANSPORTER1 | FD22 |
| Obj23 | MEDICINE PACKET | WP023 | TRANSPORTER2 | FD23 |
| Obj24 | SCALE | WS024 | SCALE | FD24 |
| Obj25 | PACKAGE | PK025 | DESTINATION | FD25 |
| .. | .. | .. | .. | .. |

142b

OBJECT DATA

Fig. 16

| TYPE OF SECOND OBJECT (Obj2) | TYPE OF FIRST OBJECT (Obj1) | | | | |
|---|---|---|---|---|---|
| | SOURCE | TRANSPORTER1 | TRANSPORTER2 | SCALE | DESTINATION |
| SOURCE | NO UPDATE | | | | |
| TRANSPORTER 1 | Obj1: NO UPDATE<br>Obj2: ADD<br>ATTRIBUTES OF Obj1 | NO UPDATE | | | |
| TRANSPORTER 2 | Obj1: NO UPDATE<br>Obj2: ADD<br>ATTRIBUTES OF Obj1 | Obj1: ELIMINATE<br>Obj2: ADD<br>ATTRIBUTES OF Obj1 | NO UPDATE | | |
| SCALE | NO UPDATE | NO UPDATE | Obj1: ADD<br>MEASURED VALUE<br>Obj2: NO UPDATE | NO UPDATE | |
| DESTINATION | NO UPDATE | Obj1: ELIMINATE<br>Obj2: ADD<br>ATTRIBUTES OF Obj1 | Obj1: ELIMINATE<br>Obj2: ADD<br>ATTRIBUTES OF Obj1 | Obj1: NO UPDATE<br>Obj2: ADD<br>MEASURED VALUE | NO UPDATE |

144b

ATTRIBUTE CONTROL TABLE

Fig. 20

| OBJECT ID | NAME | PATIENT ID | DOSAGE | FEATURE QUANTITY | |
|---|---|---|---|---|---|
| Obj31 | Mr./Ms. XX | | | FD31 | } PERSON DATA |
| Obj32 | Mr./Ms. YY | | | FD32 | |
| .. | .. | | | .. | |
| Obj35 | X1 TABLET | Obj31 | 2 TABLETS/ AFTER EACH MEAL | FD35 | } PRESCRIPTIVE MEDICINE DATA |
| .. | .. | .. | .. | .. | |

142c

OBJECT DATA

| OBJECT ID | ATTRIBUTE | TIME |
|---|---|---|
| Obj31 | SB31_2 TABLETS | T31 |
| Obj31 | SB31_2 TABLETS | T32 |
| Obj31 | SB31_2 TABLETS | T33 |

HISTORY DATA

Fig. 25

| OBJECT ID | NAME | PRODUCT NUMBER | TYPE | FEATURE QUANTITY |
|---|---|---|---|---|
| Obj41 | MINCED MEAT | MM041 | SOURCE | FD41 |
| Obj42 | BLACK PEPPER BOTTLE | PP042 | SOURCE | FD42 |
| Obj43 | LADLE | LD043 | TRANSPORTER | FD43 |
| Obj44 | BOWL | BW044 | CONTAINER | FD44 |
| Obj45 | FRYING PAN | FP045 | CONTAINER | FD45 |
| Obj46 | TRAY | TR046 | CONTAINER | FD46 |
| : | : | : | : | : |
| Obj50 | FOOD | FI050 | FOOD_ITEM | (FD50) |
| : | : | : | : | : |

142d

OBJECT DATA

Fig. 26

144d ATTRIBUTE CONTROL TABLE

| TYPE OF SECOND OBJECT (Obj2) | TYPE OF FIRST OBJECT (Obj1) | | | |
|---|---|---|---|---|
| | SOURCE | TRANSPORTER | CONTAINER | FOOD_ITEM |
| SOURCE | NO UPDATE | | | |
| TRANSPORTER | Obj1: NO UPDATE<br>Obj2: ADD ATTRIBUTE OF Obj1 | NO UPDATE | | |
| CONTAINER | Obj1: NO UPDATE<br>Obj2: GENERATE Obj3<br>(IF NOT GENERATED)<br>Obj3: ADD ATTRIBUTE OF Obj1/<br>Obj1/ UPDATE FEATURE QUANTITIES | Obj1: ELIMINATE<br>Obj2: GENERATE Obj3<br>(IF NOT GENERATED)<br>Obj3: ADD ATTRIBUTE OF Obj1/<br>UPDATE FEATURE QUANTITIES | | |
| FOOD_ITEM | Obj1: NO UPDATE<br>Obj2: ADD ATTRIBUTE OF Obj1/<br>UPDATE FEATURE QUANTITIES | Obj1: ELIMINATE<br>Obj2: ADD ATTRIBUTE OF Obj1/<br>UPDATE FEATURE QUANTITIES | Obj1: ELIMINATE<br>Obj2: ADD ATTRIBUTE OF Obj1/<br>UPDATE FEATURE QUANTITIES QUANTITIES | Obj1: ELIMINATE<br>Obj2: ADD ATTRIBUTE OF Obj1/<br>UPDATE FEATURE QUANTITIES |

INFORMATION PROCESSING DEVICE AND AN INFORMATION PROCESSING METHOD

TECHNICAL FIELD

The present disclosure relates to an information processing device, and an information processing method.

BACKGROUND ART

In the medical field, to prevent errors from occurring in medical practices, such as medicine preparation and injection of medicine into patients, many efforts have been made. For example, in preparing liquid medicines for an injection of a Ringer's solution, doctors or nurses have copied down the names and amounts of liquid medicines injected into Ringer's solution bags on the Ringer's solution bags, with a writing tool including a marker pen. Patent Literature 1 below suggests writing, as a history, data in which identifiers of operators, patients, and used medical tools and times are associated with one another to prevent improper medical practices when medical practice is carried out.

Tracing the history of actions is important for other fields as well as the medical field. For example, in the field of food processing, efforts that enable history data for processing processes to be written and the history later traced have been made for the purpose of hygiene or maintaining the quality of a product.

CITATION LIST

Patent Literature

PTL 1: JP 2009-289067A

SUMMARY

Technical Problem

Many existing efforts to trace history data need labor on screens for inputting data, etc. However, a way of requiring the labor entails risks of input mistakes of data or intentional incorrect input. Further, forcing operators to input data in addition to their normal responsibilities puts pressure on the operators. According to the scheme described in Patent Literature 1, data input is automated through introduction of a special terminal device connected to medical tools. However, because the scheme is based on the presence of the special terminal device, its application scope is limited.

Regarding this, a way of recording pictures of actions as a history is considered. In this case, labor is not needed to record the history. However, simply recording the pictures complicates later recognition of the details of actions used for containers whose contents are indeterminable from the outside.

Solution to Problem

According to one embodiment, an information processing device is provided that includes an attribute control unit that changes an association between a detected object and an attribute stored in association with the detected object in response to a detected physical action between the detected object and another detected object.

According to an information processing method, the method includes storing in memory an attribute in an association with a detected object; and changing with an attribute control unit the association between the detected object and the attribute in response to a detected physical action between the detected object and another detected object.

According to another information processing device embodiment, the device includes an interface that exchanges data with an attribute control unit that changes an association between a detected object and an attribute stored in association with the detected object in response to a detected physical action between the detected object and another detected object; and a display control unit that overlays attribute data adjacent to said detected object on a user interface unit.

Advantageous Effects of Invention

According to technology relating to an example of the disclosure, it is possible to more easily manage the details of actions as a history without putting excessive pressure on operators.

BRIEF DESCRIPTION OF DRAWINGS

FIG. 7 is an explanatory diagram for describing one example of output images shown for one embodiment.

FIG. 8 is an explanatory diagram for describing one example of object data in a first example.

FIG. 9 is an explanatory diagram for describing one example of an attribute control table in a first example.

FIG. 10B is a second half of an explanatory diagram for describing one example of the state transition of attribute data in a first example.

FIG. 11 is an explanatory diagram for describing one example of attribute data in a first example.

FIG. 15 is an explanatory diagram for describing one example of object data in a second example.

FIG. 20 is an explanatory diagram for describing one example of object data in a third example.

FIG. 21 is an explanatory diagram for describing one example of history data in a third example.

FIG. 25 is an explanatory diagram for describing one example of object data in a fourth example.

FIG. 26 is an explanatory diagram for describing one example of an attribute control table in a fourth example.

DESCRIPTION OF EXAMPLES

Figure 1:
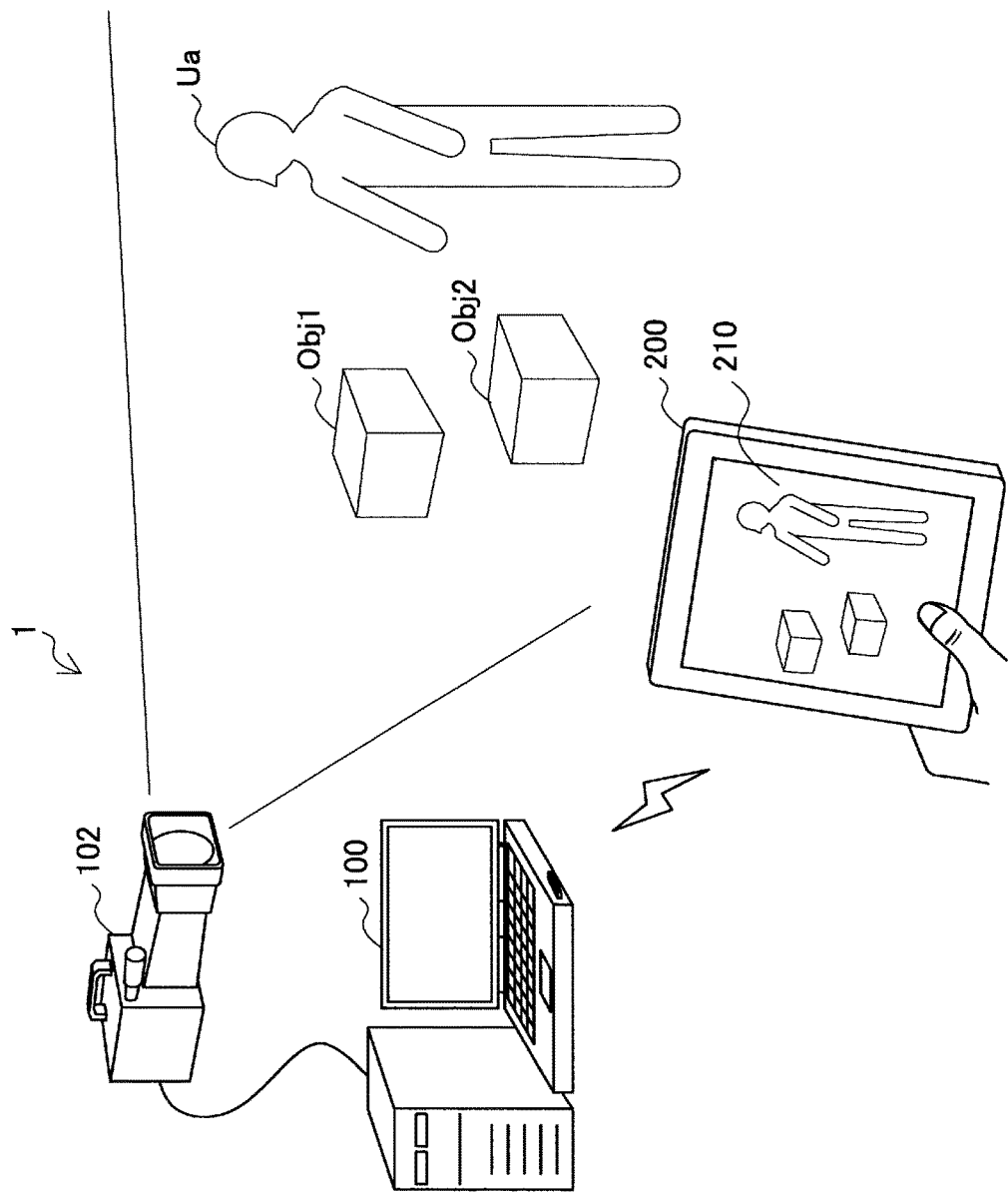
FIG. 1 is an explanatory diagram for describing an overview of an image processing system according to one embodiment.

Hereinafter, preferred examples of the present disclosure will be described in detail with reference to the appended drawings. Note that, in this specification and the appended drawings, structural elements that have substantially the same function and structure are denoted with the same reference numerals, and repeated explanation of these structural elements is omitted.

Further, description is made in the following order.
1. Overview of a system
2. Constitutional examples of an image processing device
2-1. Hardware configuration
2-2. Functional configuration
3. Constitutional examples of a terminal device
3-1. Hardware configuration
3-2. Functional configuration
4. First example
5. Second example
6. Third example
7. Fourth example
8. Variation
9. Conclusion 1. Overview of a System FIG. 1 is an explanatory diagram for describing an overview of an image processing system according to one embodiment. Referring to FIG. 1, an image processing system 1 is illustrated as one example. The image processing system 1 includes an image processing device 100 and a terminal device 200.

The image processing device 100 has an imaging unit 102. The lens of the imaging unit 102 faces objects involved in any actions in an actual space. In the example in FIG. 1, a person Ua performs an action intended for one or both of objects Obj1 and Obj2, which are present in the actual space. In addition to the objects Obj1 and Obj2, the person Ua may also be treated as one of objects. The imaging unit 102 captures actions in which the objects take part, and generates captured images (typically, each frame composing moving pictures). The generated captured images are input images to image processing performed by the image processing device 100 intended for managing a history of actions.

The terminal device 200 has an imaging unit (not shown) and a display unit 210. The terminal device 200 captures any object using the imaging unit, and requests the image processing device 100 to distribute data that is associated with objects in images. In addition, the terminal device 200 displays data sent from the image processing device 100 on the display unit 210. Data sent from the image processing device 100 enables a history of actions taken for several objects to be recognized later. For example, the history of actions can be recognized through attributes associated with the objects or can be recognized from history data itself for which a timestamp is given.

In FIG. 1, the image processing device 100 and the terminal device 200 show an example formed as devices that are physically different. However, the image processing device 100 and the terminal device 200 may be formed as an integrated device. The image processing device 100 and the terminal device 200 may each be general devices, for example desktop PCs, tablet PCs, notebook PCs, smart phones, or PDAs, or may be dedicated devices intended for management/reading of the history. In addition, the screen of the terminal device 200 may be realized with a head mount display.

2. Constitutional Examples of an Image Processing Device (2-1. Hardware Configuration)

Figure 2:
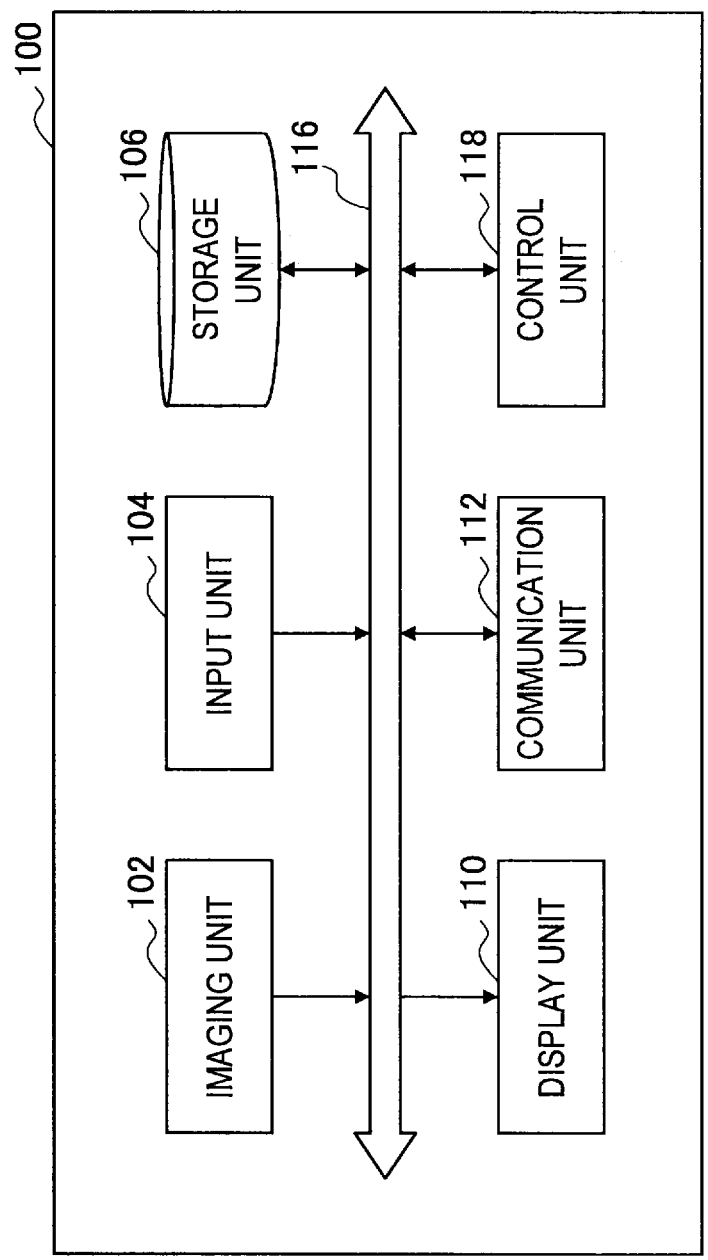
FIG. 2 is a block diagram illustrating one example of a hardware configuration of an image processing device according to one embodiment.

FIG. 2 is a block diagram illustrating one example of the hardware configuration of an image processing device 100 according to one embodiment. Referring to FIG. 2, the image processing device 100 includes an imaging unit 102, an input unit 104, a storage unit 106, a display unit 110, a communication unit 112, a bus 116 and a control unit 118.

(1) Imaging Unit

The imaging unit 102 is a camera module that captures images. The imaging unit 102 captures subjects with imaging elements, such as a CCD (Charge Coupled Device) or a CMOS (Complementary Metal Oxide Semiconductor), and generates captured images. The imaging unit 102 may not always be part of the imaging processing device 100. For example, as in the example of FIG. 1, an imaging device connected in a wired or wireless manner to the image processing device 100 may be treated as the imaging unit 102.

(1) Input Unit

The input unit 104 is an input device, which is used by a user to operate the image processing device 100 or input information to the image processing device 100. For example, the input unit 104 may include a touch sensor, which detects touch by a user onto the screen of the display unit 110. Instead (or in addition), the input unit 104 may include a pointing device, such as a mouse or a touch pad. Further, the input unit 104 may include other input devices, such as a keyboard, a keypad, buttons, a switch or a remote controller.

(3) Storage Unit

The storage unit 106 includes a storage medium, such as a semiconductor memory or a hard disc, and stores programs and data to process with the image processing device 100. The data stored in the storage unit 106 can include, for example, captured image data generated by the imaging unit 102 and various data in a database, which will be described later. In addition, a portion or all of programs and data in the specification may be acquired from external data sources (e.g. data servers, network storages or external memories, etc.) without being stored in the storage unit 106.

(4) Display Unit

The display unit 110 is a display module consisting of an LCD (Liquid Crystal Display), an OLED (Organic Light-Emitting Diode) or a CRT (Cathode Ray Tube). In addition, the display unit 110 may not always be part of the image processing device 100. For example, a display device connected in a wired or wireless manner to the image processing device 100 may be treated as the display unit 110.

(5) Communication Unit

The communication unit 112 is a communication interface, which relays communication between the image processing device 100 and other devices (e.g. the terminal device 200). The communication unit 112 supports any wireless or wired communication protocols and establishes communication connections with other devices.

(7) Bus

The bus 116 connects the imaging unit 102, the input unit 104, the storage unit 106, the display unit 110, the communication unit 112 and the control unit 118 to one another.

(8) Control Unit

The control unit 118 corresponds to a processor, such as a CPU (Central Processing unit) or a DSP (Digital Signal Processor). The control unit 118 executes programs stored in the storage unit 106 or other storage media to operate various functions of the image processing device 100, which will be described later.

(2-2. Functional Configuration)

Figure 3:
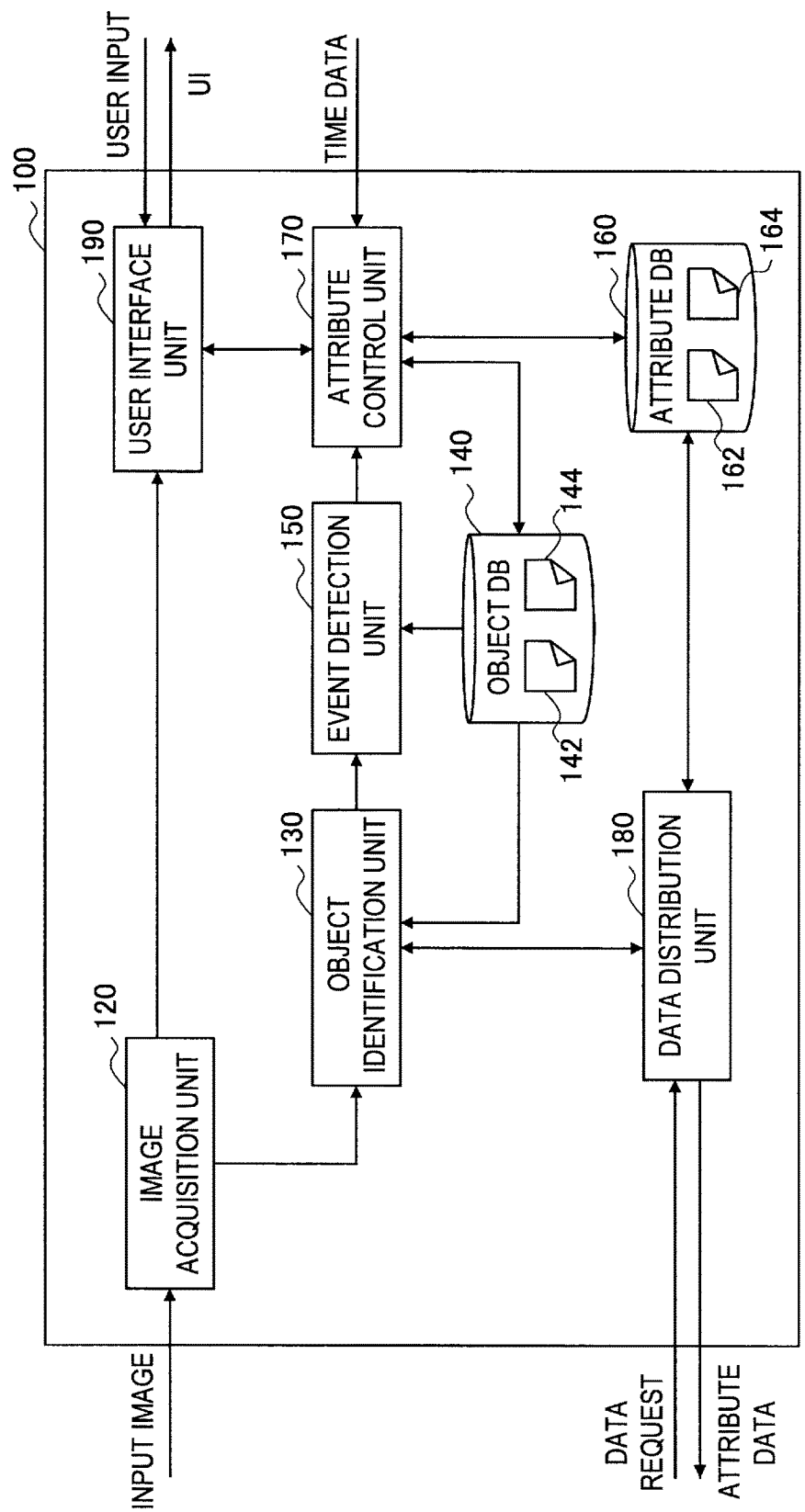
FIG. 3 is a block diagram illustrating one example of a logical functional configuration of an image processing device according to one embodiment.

FIG. 3 is a block diagram illustrating one example of the logical functional configuration realized by the storage unit 106 and the control unit 118 of the image processing device 100 shown in FIG. 2. Referring to FIG. 3, the image processing device 100 includes an image acquisition unit 120, an object identification unit 130, an object database (DB) 140, an event detection unit 150, an attribute DB 160, an attribute control unit 170, a data distribution unit 180 and a user interface unit 190.

(1) Image Acquisition Unit

The image acquisition unit 120 acquires captured images generated by the imaging unit 102 as input images. In the input images, objects involved in medical practices, food processing actions or other actions appear. A series of input images acquired by the image acquisition unit 120 typically includes moving pictures. The image acquisition unit 120 sequentially outputs the acquired input images to the object identification unit 130.

(2) Object Identification Unit

The object identification unit 130 identifies objects present in the actual spaces from input images. The object identification unit 130 may identify objects in the input images, for example, by combining image feature quantities extracted from the input images with image feature quantities previously extracted for each object. In addition, the object identification unit 130 may identify objects in the input images by interpreting identification information, such as barcodes attached to, and printed or mounted on each object, or 2D codes (e.g. QR Code (registered trademark)). In addition, the object identification unit 130 may identify objects in the input images by reading character strings or labels from the surface of each object. In addition, persons in the input images are also identified as an object in one example, which will be described later. For example, identifying the persons can be performed with feature quantities of face images previously extracted. In this embodiment, the identification of the objects by combination of the image feature quantities is mainly described as one example.

(3) Object DB

The object DB 140 is a database that stores data relating to objects involved in actions as a target of history management. The data stored in the object DB 140 can be used to identify objects by the object identification unit 130, detect events by the event detection unit 150 and control the attributes of the objects by the attribute control unit 170. In this embodiment, the object DB 140 stores object data 142 including at least known image feature quantities of each object. Further, the object DB 140 can store an attribute control table 144, which defines the control patterns of the attributes. Particular examples of such data are described later.

(4) Event Detection Unit

The event detection unit 150 detects events corresponding to physical acts between the plurality of objects identified by the object identification unit 130 using the input images. In this specification, the physical acts between the objects indicate any act in the actual space between the plurality of objects (which can include both real objects and persons) involved in actions. For example, contact or approach of two objects can correspond to physical acts between these objects. An operation intended for any real object of any person can also correspond to physical acts between a corresponding person and a corresponding object. Events corresponding to these physical acts become the trigger for the processing that should be performed in response to the physical acts described above in the actual spaces. Whether an event should be detected relating to a physical act can be defined according to the use of an application. Events relating to the following physical acts are detected in four examples, which will be described later.

First example) Transportation of liquid medicine in medical practice

Second example) Combination of medicine in medicine preparation

Third example) Ingestion of medicine by patients

Fourth example) Mixing food materials and seasoning in food processing actions

In addition, these are merely examples for description, and events relating to physical acts between objects in other actions may be detected.

(5) Attribute DB

The attribute DB 160 is a database that stores data to enable a history of actions taken for each object to be recognized. The data stored in the attribute DB 160 is managed by an attribute control unit 170, which will be described later. In this embodiment, the attribute DB 160 stores attribute data 162, which represents attributes associated with each object. The attribute data 162 can represent both initial attributes previously associated with some objects and later attributes associated with the other objects in response to the detection of the events described above. By reading such attribute data 162, the history of actions taken for each object can be recognized. Further, the attribute DB 160 can store history data 164, which represents transition of the attributes of each object for each event described above.

(6) Attribute Control Unit

The attribute control unit 170 controls attributes associated with each object. For example, in this embodiment, in response to the detection of the event described above by the event detection unit 150, the attribute control unit 170 associates attribute data, which is associated with a first object involved in a physical act corresponding to the detected event, with a second object.

Figure 4:
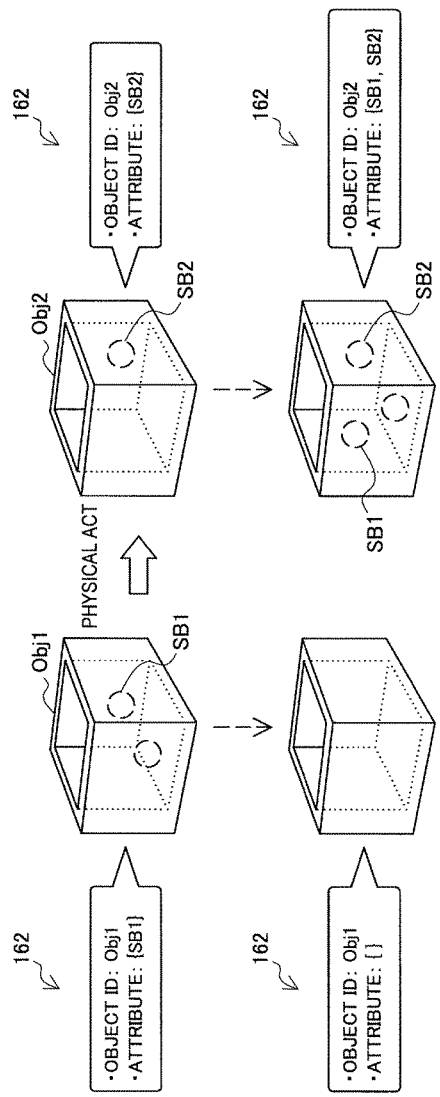
FIG. 4 is an explanation diagram for describing a basic concept of control of attributes in one embodiment.

FIG. 4 is an explanatory diagram for describing a basic concept of control of attributes in this embodiment. Referring to FIG. 4, two objects Obj1 and Obj2 involved in physical acts are shown. These two objects are typically objects capable of containing a substance. In this specification, containing a substance includes various types of actions, such as receiving a substance inside, maintaining a substance portably, and holding a substance as a component. For example, in the upper half of FIG. 4, the object Obj1 contains a substance SB1 and the object Obj2 contains a substance SB2. In this case, in the attribute data 162, an attribute value representing the kind of the substance SB1 is associated with the object Obj1 and another attribute value representing the kind of the substance SB2 is associated with the object Obj2. In addition, the attribute control unit 170 newly associates the attribute value associated with the object Obj1 with the object Obj2 if an event corresponding to a physical act from the object Obj1 to the object Obj2 is detected. In several examples, the direction of the movement of such an attribute value can be determined by the attribute control unit 170 with reference to the attribute control table 144 described above. In the lower half of FIG. 4, as a result of detecting an event corresponding to a physical act, an attribute value representing the kind of the substance SB1 is newly associated with the object Obj2. Alternatively, an attribute value representing the kind of the substance SB1 is removed from the object Obj1. In addition, the attribute data of each object may represent the amount as well as the kind of the substance contained in the associated object.

(7) Data Distribution Unit

The data distribution unit 180 distributes attribute data associated with several objects to a device displaying images of those objects, and displays the sent attribute data on the screen of that device. For example, the data distribution unit 180 receives a request for data transmitted from the terminal device 200 illustrated in FIG. 1. The data request can include images captured by the terminal device 200 or feature quantities extracted from those images. The data distribution unit 180 outputs the images or the image feature quantities included in the data request to the object identifying unit 130 to allow the objects in the images to be identified. In addition, if the ID (identifier) of an object in an image captured by the terminal device 200 is included in the data request, the identification of an object by the object identification unit 130 may be omitted. Then, the data distribution unit 180 acquires attribute data associated with the object ID of the identified object from the attribute DB 160. In addition, the data distribution unit 180 distributes the acquired attribute data to the terminal device 200. The data distribution unit 180 may further distribute location data representing locations of the identified object in the image to the terminal device 200.

(8) User Interface Unit

The user interface unit 190 can provide various user interfaces to users conforming to the purpose of an application. For example, the user interface unit 190 may provide UI screens so that users can read or edit the object data 142, the attribute control table 144, the attribute data 162 or the history data 164. In addition, the user interface 190 may provide approval screens for the users to be able to receive approval from the users on update of the attribute data.

3. Constitutional Examples of a Terminal Device (3-1. Hardware Configuration)

Figure 5:
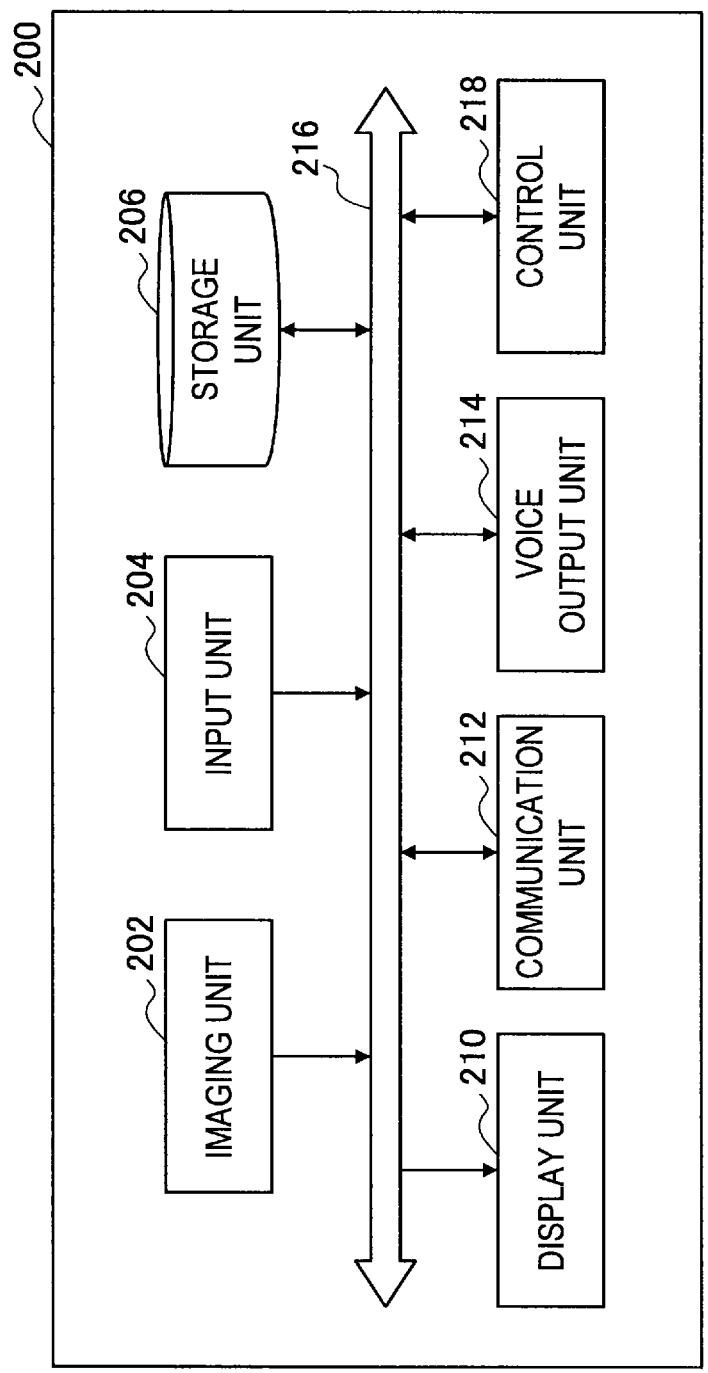
FIG. 5 is a block diagram illustrating one example of a hardware configuration of a terminal device according to one embodiment.

FIG. 5 is a block diagram illustrating one example of the hardware configuration of a terminal device 200 according to one embodiment. Referring to FIG. 5, the terminal device 200 includes an imaging unit 202, an input unit 204, a storage unit 206, a display unit 210, a communication unit 212, a voice output unit 214, a bus 216 and a control unit 218.

(1) Imaging Unit

The imaging unit 202 is a camera module that captures images. The imaging unit 202 captures subjects with imaging elements, such as a CCD or a CMOS, and generates captured images. The imaging unit 202 may not always be part of the terminal device 200. For example, an imaging device connected in a wired or wireless manner to the terminal device 200 may be treated as the imaging unit 202.

(2) Input Unit

The input unit 204 is an input device, which is used by a user to operate the terminal device 200 or input information to the terminal device 200. For example, the input unit 204 may include a touch sensor, which detects touch by a user on the screen of the display unit 210. Instead (or in addition), the input unit 204 may include a pointing device, such as a mouse or a touch pad. Further, the input unit 204 may include other input devices, such as a keyboard, a keypad, buttons, a switch or a remote controller.

(3) Storage Unit

The storage unit 206 includes a storage medium, such as a semiconductor memory or a hard disk, and stores programs and data to process with the terminal device 200. The data stored in the storage unit 206 can include, for example, data sent from the image processing device 100 described above. In addition, a portion or all of programs or data in the specification may be acquired from external data sources (e.g. data servers, network storages or external memories, etc.) without being stored by the storage unit 206.

(4) Display Unit

The display unit 210 is a display module including an LCD, an OLED or a CRT. In addition, the display unit 210 may not always be part of the terminal device 200. For example, a display device connected in a wired or wireless manner to the terminal device 200 may be treated as the display unit 210.

(5) Communication Unit

The communication unit 212 is a communication interface, which moderates communication between other devices (e.g. the image processing device 100) and the terminal device 200. The communication unit 212 supports any wireless or wired communication protocol and establishes communication connection with other devices.

(6) Voice Output Unit

The voice output unit 214 is a voice output module, which includes a speaker, for example. In addition, the voice output unit 214 may not always be part of the terminal device 200. For example, a voice output unit connected in a wired or wireless manner to the terminal device 200 may be treated as the voice output unit 214.

(7) Bus

The bus 216 connects the imaging unit 202, the input unit 204, the storage unit 206, the display unit 210, the communication unit 212, the voice output unit 214 and the control unit 218 to one another.

(8) Control Unit

The control unit 218 corresponds to a processor, such as a CPU or a DSP. The control unit 218 executes programs stored in the storage unit 206 or other storage media to operate various functions of the terminal device 200, which will be described later.

(3-2. Functional Configuration)

Figure 6:
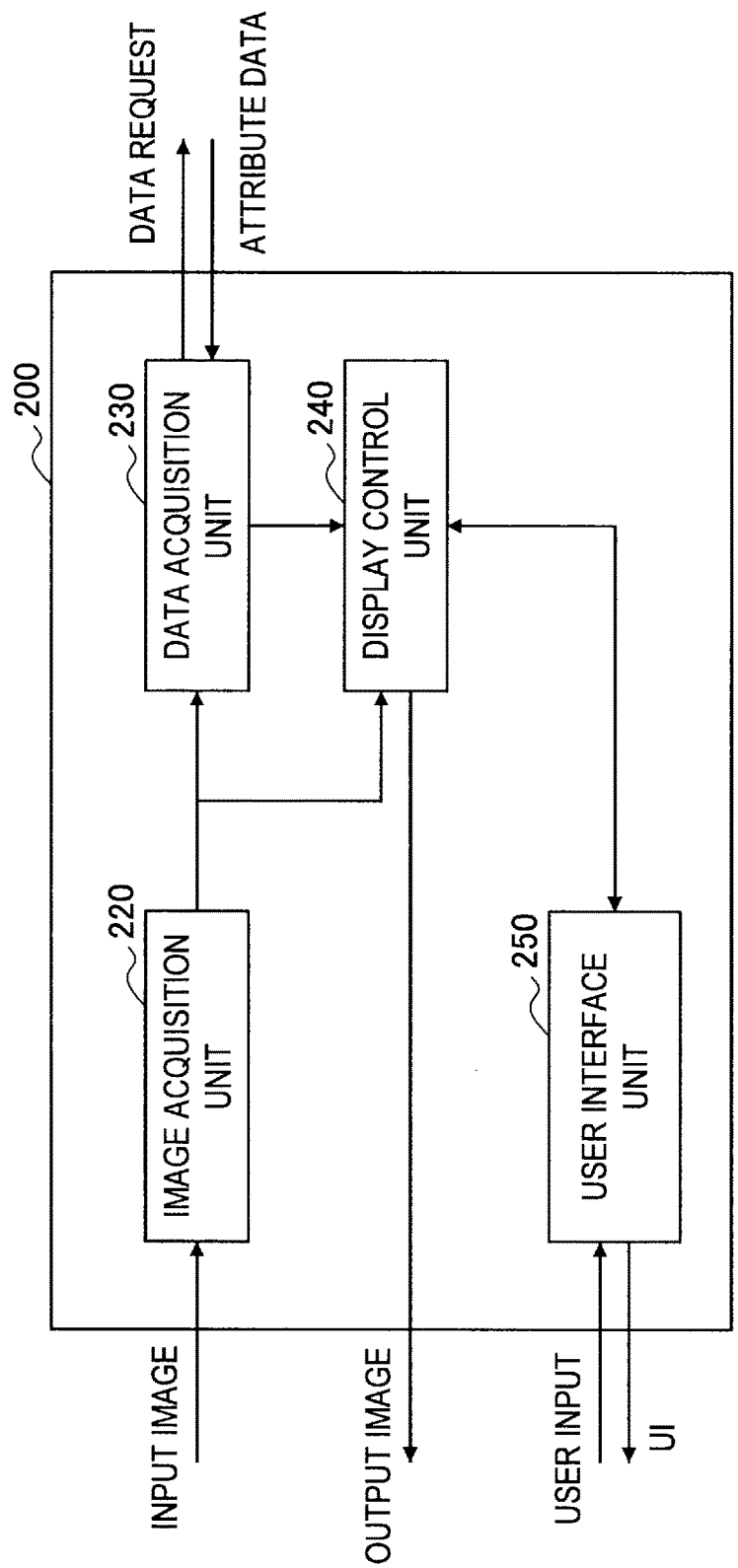
FIG. 6 is a block diagram illustrating one example of a logical functional configuration of a terminal device according to one embodiment.

FIG. 6 is a block diagram illustrating one example of the logical functional configuration realized by the storage unit 206 and the control unit 218 of the terminal device 200 shown in FIG. 5. Referring to FIG. 6, the terminal device 200 includes an image acquisition unit 220, a data acquisition unit 230, a display control unit 240 and a user interface unit 250.

(1) Image Acquisition Unit

The image acquisition unit 220 acquires captured images generated by the imaging unit 202 as input images. In the input images, various objects present in the actual space appear. The image acquisition unit 220 sequentially outputs the acquired input images to the data acquisition unit 230 and the display control unit 240.

(2) Data Acquisition Unit

The data acquisition unit 230 acquires attribute data associated with objects identified in the input images acquired by the image acquisition unit 220. For example, the data acquisition unit 230 transmits requests for data including the input images or the image feature quantities of the input images to the image processing device 100. The data acquisition unit 230 identifies the objects in the input images and may include the object ID of the identified object in the data request. In addition, the data acquisition unit 230 can acquire attribute data sent from the image processing device 100 in response to the data request. In addition to the attribute data, location data representing the location of the identified object in the image may be further acquired from the image processing device 100. In addition, the data acquisition unit 230 outputs the acquired attribute data (and the location data) to the display control unit 240.

In this embodiment, the attribute data acquired from the data acquisition unit 230 can include attribute data associated with a second object involved in a physical act with a first object. That attribute data may be data which is associated with the first object before an event corresponding to a physical act is detected, and newly associated with the second object in response to the detection of such event. In other words, by reading the attribute data acquired by the data acquisition unit 230, the details of the actions taken for the object in an input image can be recognized. In addition, the attribute data acquired from the image processing device 100 may be represented in a type of history data given in a timestamp.

(3) Display Control Unit

The display control unit controls the display of images and data in the terminal device 200. For example, if attribute data associated with objects in input images is acquired by the data acquisition unit 230, the display control unit 240 overlaps the acquired attribute data with the input images. The attribute data may be represented along with object IDs or the names of the objects without depending on the location of associated objects. Instead, the attribute data may be represented to be overlaid on the location of the associated object in the image or to represent the location.

FIG. 7 is an explanatory diagram for describing one example of output images shown for one embodiment. On the left of FIG. 7, an input image Im00 is illustrated as one example that can be imaged by the terminal device 200. In the input image Im00, an object Obj2 appears. The terminal device 200 transmits a data request, requesting data to be overlapped with the input image Im00, to the image processing device 100, and receives data sent from the image processing device 100. On the right of FIG. 7, an output image Im01 is illustrated as one example that can be displayed by the terminal device 200. The output image Im01 is generated by overlapping a virtual object, a message MSG1, with the input image Im00. The message MSG1 is generated based on the attribute data 162 illustrated in the lower half in, for example, FIG. 4, and represents that the object Obj2 in the input image Im00 contains substances SB1 and SB2. The user of the terminal device 200 can recognize by viewing the output image Im01, for example, that an action of adding the substances SB1 and SB2 to the object Obj2 has been performed. In addition, voice reading of the message MSG1 may be output through the voice output unit 214 instead of the message MSG1 being displayed by the display control unit 240 through the display unit 210.

(4) User Interface Unit

The user interface unit 250 can provide various user interfaces to users conforming to the purpose of an application. For example, the user interface unit 250 may provide UI screens to clearly indicate that the attribute data is acquired by the data acquisition unit 230 from a user.

So far, conceptual description of one embodiment according to the disclosure has been given. In four examples of the following paragraphs, particular application situations of technology according to the disclosure will be respectively discussed and new details according to the technology will be described.

4. First Example

In the first example, the transportation of liquid medicine in medical practice is illustrated as a target of history management. Accordingly, the image processing device 100 detects events corresponding to physical acts between medical tools that persons such as doctors, nurses or pharmacists use to deal with liquid medicine.

(1) Example of Objects

FIG. 8 is an explanatory diagram for describing one example of object data in the first example. Referring to FIG. 8, object data 142a is illustrated as one example stored in the object DB 140. The object data 142a includes five data items that are called "Object ID," "Name," "Product Number," "Type" and "Feature Quantity."

"Object ID" is an identifier for immediately identifying each object. "Name" represents a name given to each object. In the example of FIG. 8, as names, "vial" is given to an object Obj11, "Syringe" is given to an object Obj12 and "Ringer's Solution Bag" is given to an object Obj13. "Product Number" represents character strings given to individually distinguish the same kinds of objects.

"Type" is an item referred to in controlling attributes by the attribute control unit 170 and at least one of a plurality of types of candidates is defined for each object. In this example, some of the following three types of candidates are assigned to each object.

"SOURCE" . . . A type representing the object of the transportation source of a substance "TRANSPORTER" . . . A type representing an object capable of transporting the substance "DESTINATION" . . . A type representing the object of a transportation destination of the substance In the example of FIG. 8, the type of the object Obj11 is "SOURCE," the type of the object Obj12 is "TRANSPORTER," and the type of the object Obj11 is "DESTINATION."

"Feature Quantity" is extracted from a known image for each object. The object identification unit 130 combines image feature quantities extracted from an input image with such feature quantities of the object data 142a, and can identify objects in the input image.

(2) Event

In this example, the event detection unit 150 detects events corresponding to physical acts between medical tools identified by the object identification unit 130. For example, the following events can be discussed as events in which the objects illustrated in FIG. 8 take part.

Event Ev11) Injection of liquid medicine to syringe from vial

Event Ev12) Injection of liquid medicine to a Ringer's solution bag from the syringe These events may be detected if given event detecting conditions on, for example, two events are satisfied. The given event detecting conditions may be some of the following conditions.

Condition C11) The distance between two objects is lower than a threshold value.

Condition C12) The time during which the condition C11 has been continuously satisfied is over a threshold value.

Condition C13) A given gesture of a person with respect to two objects is identified.

The distance in the condition C11 may be a 2D distance in an input image or a 3D distance in an actual space, which is recognized based on known 3D structure recognizing technology. Threshold values for the conditions C11 and C12 may be defined in common without depending on objects or individually for each object.

If events corresponding to physical acts between a plurality of objects are detected according to the event detecting conditions described above, the event detection unit 150 notifies the attribute control unit 170 of the detected event.

(3) Control on Attributes

In this example, if the types defined for objects involved in in the detected events satisfy given attribute control conditions, the attribute control unit 170 changes the attributes of those objects. The attribute control conditions are defined in an attribute control table described above.

FIG. 9 is an explanatory diagram for describing one example of an attribute control table in the first example. Referring to FIG. 9, the attribute control table 144a is represented as one example stored in the object DB 140. The attribute control table 144a is defined in a matrix form with three types of objects in both columns and rows. Each column corresponds to the type of a first object involved in an event. Each row corresponds to the type of a second object involved in the event.

For example, if the type of the first object is "SOURCE" and the type of the second object is "TRANSPORTER," then an attribute associated with the first object is added to (or newly associated with) the second object. The attribute of the first object is not updated.

In addition, if the type of the first object is "TRANSPORTER," and the type of the second object "DESTINATION," then the attribute associated with the first object is added to the second object. The attribute of the first object is eliminated.

For combinations of other types, the attributes of the first and second objects are not updated.

In other words, if an event is detected by the event detection unit 150, then the attribute control unit 170 specifies an object involved in the detected event, and determines the control content of the attribute corresponding to the combination of the types of the specified object by referring to the attribute control table 144a. In addition, the attribute control unit 170 updates the attribute data 162 stored in the attribute DB 160 according to the determined control content. The update of the attribute data 162 at this point can include the association of new attributes with the specified object and the elimination of the attributes of the specified object. In addition, the attribute control unit 170 adds a record corresponding to the detected event to the attribute data, which will be described later.

(4) Data Transition

Figure 10A:
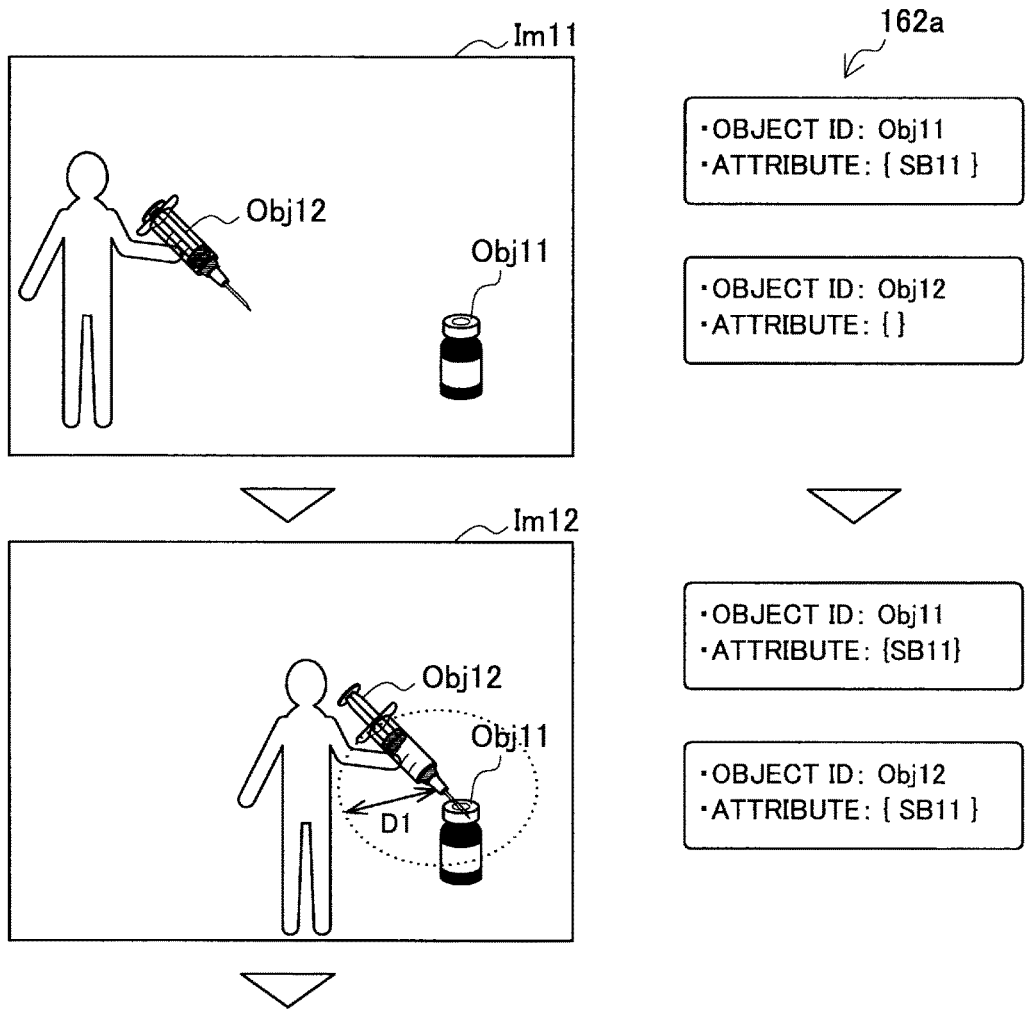
FIG. 10A is a first half of an explanatory diagram for describing one example of the state transition of attribute data in a first example.

FIGS. 10A and 10B are explanatory diagrams for describing one example of the state transition of attribute data according to an exemplary scenario in this example. On the left of the drawings, four input images Im11 to Im14 acquired in a time series are sequentially illustrated, and on the right thereof, the partial content of the attribute data 162a at each point in time is illustrated.

Referring to FIG. 10A, in the input image Im11, a vial Obj11 and a syringe Obj12 appear. For the attribute data 162a, an attribute representing a substance SB11 is associated with the vial Obj11. This represents that the substance SB11 is contained in the vial Obj11. On the other hand, no attribute value is associated with the syringe Obj12. This represents that nothing is contained in the syringe Obj12.

In addition, in the input image Im12, the syringe Obj12 appears in a range of a distance threshold value D1 from the vial Obj11. The event detection unit 150 detects an event corresponding to the extraction of liquid medicine between the vial Obj11 and the syringe Obj12, according to, for example, the event detecting condition C11 or C12 described above. According to the object data 142a, the type of the vial Obj11 is "SOURCE," and the type of the syringe Obj12 is "TRANSPORTER." The attribute control unit 170 determines the control content of the attribute corresponding to a combination of "SOURCE" and "TRANSPORTER" by referring to the attribute control table 144a, and newly associates the attribute value "SB11" associated with the vial Obj11, with the syringe Obj12. As a result, the attribute data 162a represents that the substance SB11 has been contained in the syringe Obj12.

Then, referring to FIG. 10B, in the input image Im13, the syringe Obj12 and a Ringer's solution bag Obj13 appear. For the attribute data 162a, an attribute value representing the substance SB12 is associated with the Ringer's solution bag Obj13. This is a result of an action before the scenario shown in FIGS. 10A and 10B, and represents that the substance SB12 has been contained in the Ringer's solution bag Obj13.

In addition, in the input image Im14, within a range of a distance threshold value D1 from the syringe Obj12, the Ringer's solution bag Obj13 appears. The event detection unit 150 detects an event corresponding to the injection of liquid medicine between the syringe Obj12 and the Ringer's solution bag Obj13 according to, for example, the event detecting condition C11 or C12 described above. According to the object data 142a, the type of the syringe Obj12 is "TRANSPORTER," and the type of the Ringer's solution bag Obj13 is "DESTINATION." The attribute control unit 170 determines the control content of the attribute corresponding to a combination of "TRANSPORTER" and "DESTINATION" by referring to the attribute control table 144a, and newly associates the attribute value "SB11" associated with the syringe Obj12, with the Ringer's solution bag Obj13. As a result, the attribute data 162a represents that the substance SB11 and SB12 has been contained in the Ringer's solution bag Obj13.

FIG. 11 represents the content of history data 164a as one example generated by the attribute control unit 170 between the scenarios described above. Referring to FIG. 11, the history data 164a includes four data items that are called "Object ID," "Attribute (before)," "Attribute (after)," and "Time." "Object ID" is an identifier, which identifies objects involved in a history, which each record represents. "Attribute (before)" represents the attribute value of an object before being updated by the attribute control unit 170. "Attribute (after)" represents the attribute value of an object after being updated by the attribute control unit 170. "Time" represents the detecting time of a corresponding event (or may be the update time of an attribute). The attribute control unit 170 acquires time authenticating data corresponding to these times from an external time authenticating server, and may store the acquired time authenticating data by associating the obtained time authenticating data with the history as shown in FIG. 11 to enhance the reliability of the history. In the example of FIG. 11, the update of the attribute of the syringe Obj12 at the time T11, and the update of the attributes of the syringe Obj12 and the Ringer's solution bag Obj13 at the time T12 are illustrated as the history data 164a.

(5) Example of Display

Figure 12:
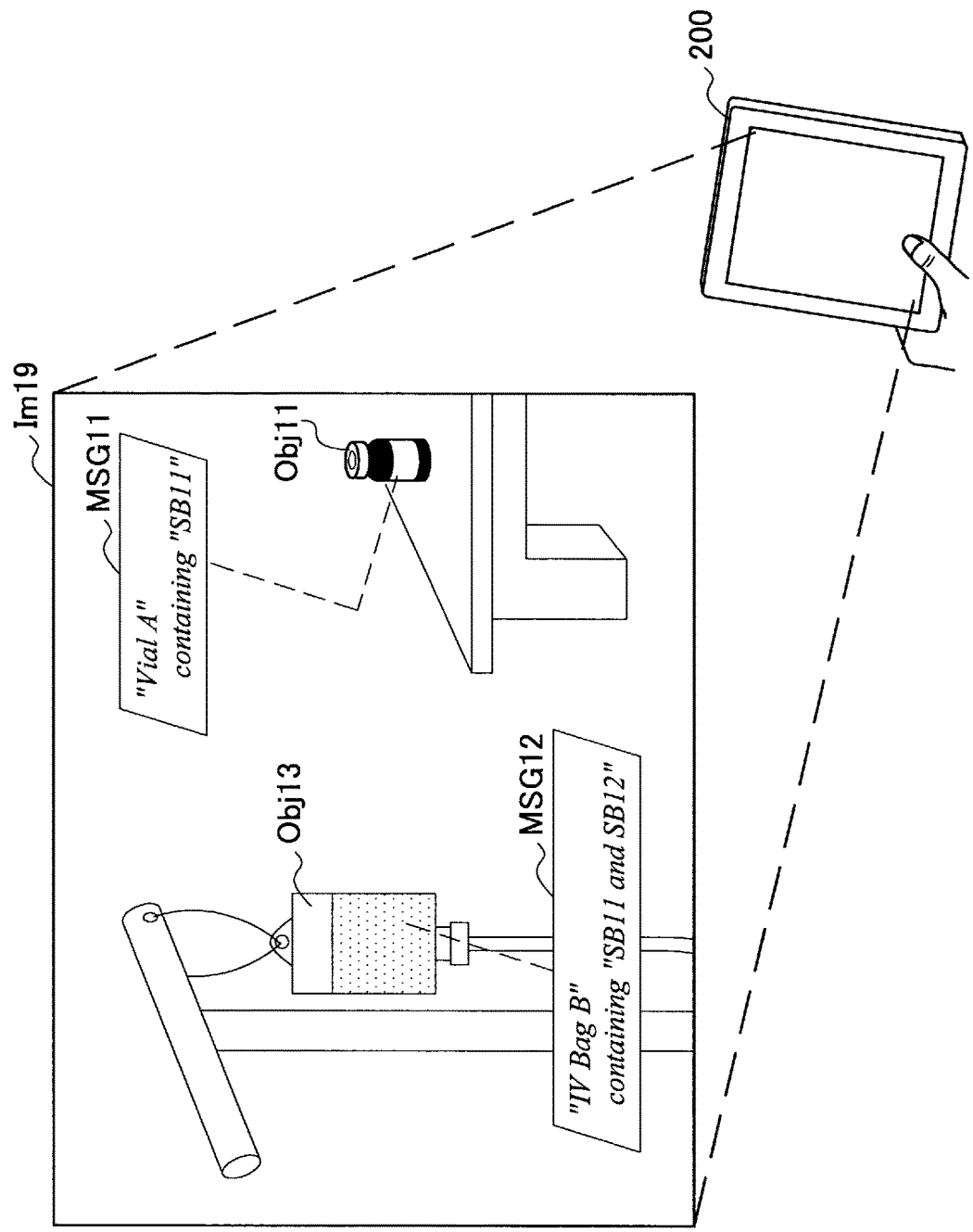
FIG. 12 is an explanatory diagram for describing one example of output images shown for a first example.

FIG. 12 is an explanatory diagram for describing one example of output images shown by the terminal device 200 for this example. Referring to FIG. 12, an output image Im19 is illustrated as one example. In addition, in the output image Im19, the vial Obj11 and the Ringer's solution bag Obj13 appear. In addition, a message MSG11 indicating the vial Obj11 and a message MSG12 indicating the Ringer's solution bag Obj13 are overlapped with the output image Im19. The message MSG11 represents that the vial Obj11 contains the substance SB11. The message MSG12 represents that the Ringer's solution bag Obj13 contains the substances SB11 and SB12. The user of the terminal device 200 can easily recognize, for example, by reading such a message MSG12, whether proper liquid medicine has been injected into the Ringer's solution bag Obj13.

(6) Flow of Processing (6-1) Attribute Control Processing

Figure 13:
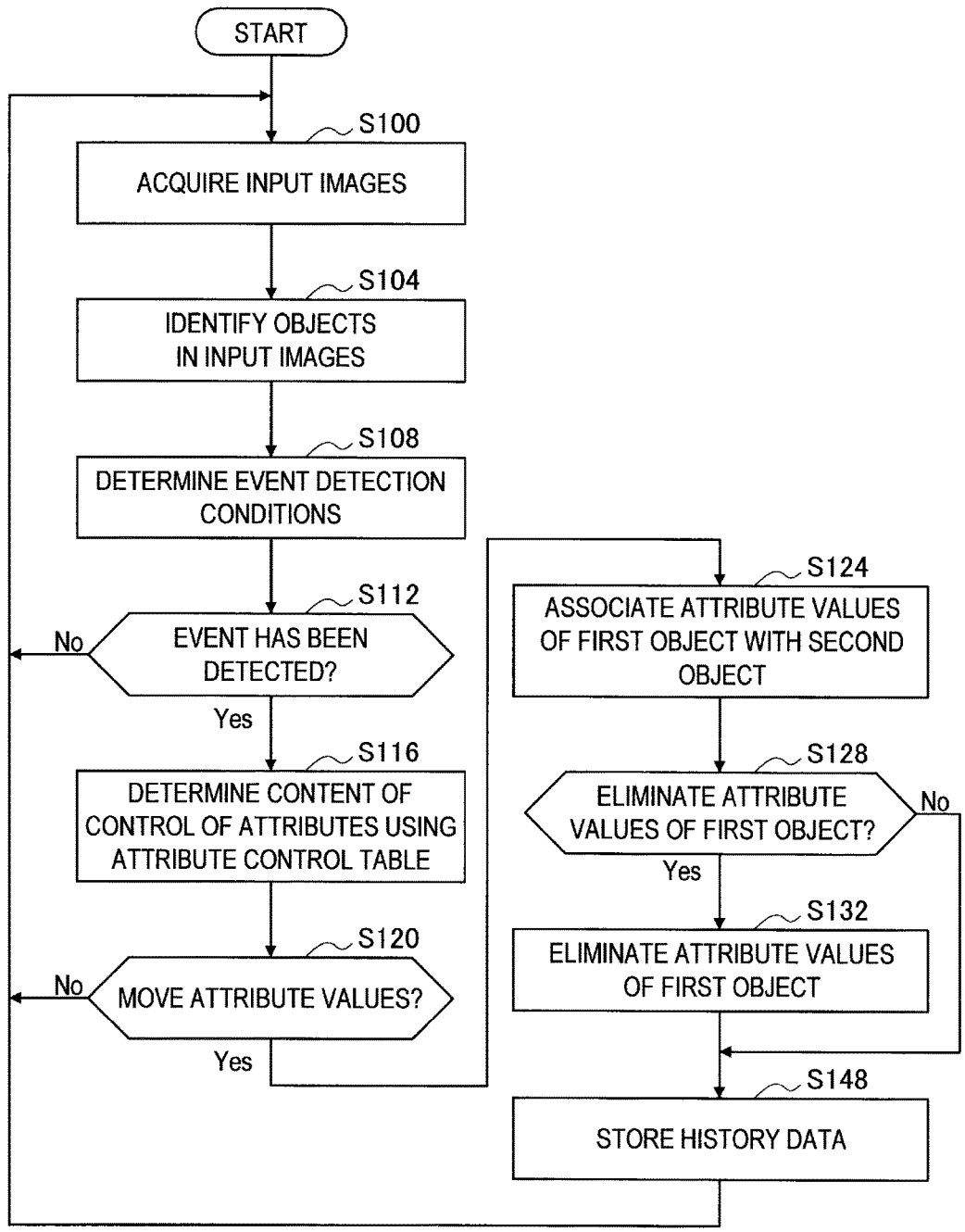
FIG. 13 is a flowchart illustrating one example of the flow of attribute control processing in a first example.

FIG. 13 is a flowchart illustrating one example of the flow of attribute control processing by the image processing device 100 in this example. The attribute control processing shown in FIG. 13 is repeated for input images sequentially acquired by the image acquisition unit 120.

First, the image acquisition unit 120 acquires captured images generated by the imaging unit 102 as input images (step S100). In addition, the image acquisition unit 120 outputs the acquired input images to the object identification unit 130.

Then, the object identification unit 130 identifies objects in the input images with known feature quantities of each object stored by the object DB 140 (step S104).

Then, the event detection unit 150 determines whether the event detecting conditions described above for the objects identified by the object identification unit 130 are satisfied (step S108). At this point, when the event detecting conditions are not satisfied, the following processing is skipped (step S112). If the event detecting conditions are satisfied, the event detection unit 150 notifies the attribute control unit 170 of the detected event.

If the event is detected by the event detection unit 150, the attribute control unit 170 determines the control content of the attributes of objects involved in the detected event using the attribute control data 144a (step S116). In addition, if it is determined to move an attribute value from a first object to a second object (step S120), then the attribute control unit 170 associates the attribute value associated with the first object, with the second object (step S124). In addition, if it is determined to eliminate the attribute value of the first object (step S128), then the attribute control unit 170 eliminates the attribute value associated with the first object (step S132).

In addition, the attribute control unit 170 stores new records of history data 164a including the attribute values before and after being updated in the attribute DB 160 (step S148).

(6-2) Display Control Processing

Figure 14:
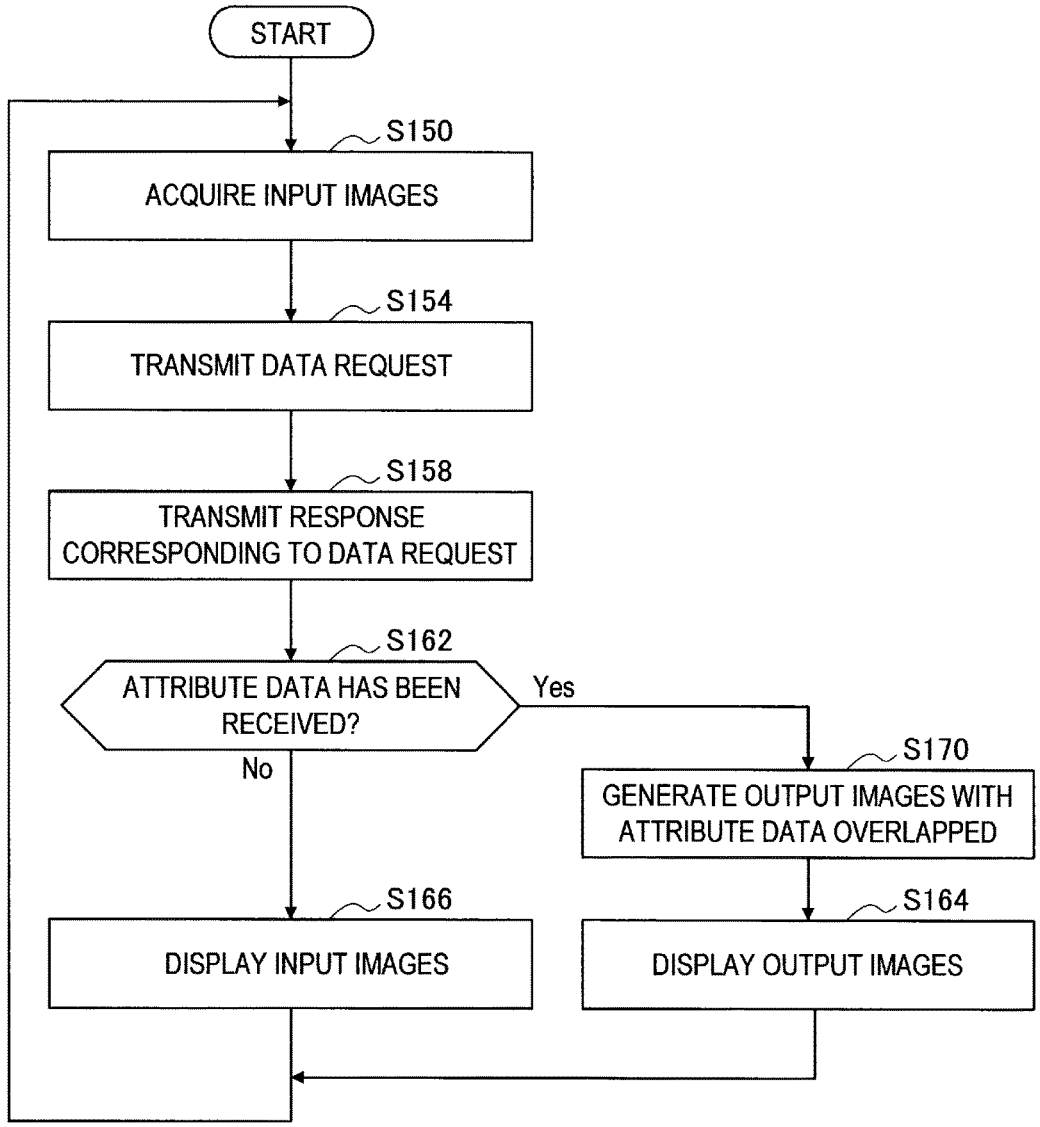
FIG. 14 is a flowchart illustrating one example of the flow of display control processing in a first example.

FIG. 14 is a flowchart illustrating one example of the flow of display control processing by the terminal device 200 in this example. The display control processing shown in FIG. 14 may be repeated for input images sequentially acquired by the image acquisition unit 220 of the terminal device 200, or be performed once for one input image acquired as a snapshot.

First, the image acquisition unit 220 acquires captured images generated by the imaging unit 202 as input images (step S150). In addition, the image acquisition unit 220 outputs the acquired input images to the data acquisition unit 230 and the display control unit 240.

Then, the data acquisition unit 230 transmits a data request, requesting attribute data associated with objects identified in the acquired input images, to the image processing device 100 (step S154). The data obtaining unit 230 receives a response corresponding to the data request from the image processing device 100 (step S158). At this point, if the attribute data described above as a response to the data request has been received, the processing proceeds to S170. On the other hand, if the attribute data has not been received, the input images are displayed by the display control unit 240 (step S166).

In S170, the display control unit 240 generates output images by overlapping the attribute data acquired by the data acquisition unit 230 with the input images (step S170). In addition, the display control unit 240 displays the output images on the display unit 210 (step S164).

So far, a first example has been described with reference to FIGS. 8 to 14. According to this example, in a state in which liquid medicine is transported from one medical tool to another medical tool, it is possible to recognize the configuration of liquid medicine contained in a medical tool through the attributes of an object.

In general, once liquid medicine is transported to a medical tool, it is difficult for persons other than the operator to know what is contained in the medical tool unless, for example, a memo is written. However, according to this example, persons other than the operator can also easily recognize what is contained in the medical tool by reading an update history of the attributes or the attribute data of an object.

In addition, there is no need for the operator in medical practices to input data when updating the attributes of an object. Accordingly, writing a history incorrectly or incorrect data due to excessive pressure on the operator is prevented.

5. Second Example

In the second example, a combination of medicine in preparing medicine is illustrated as the target of history management. Accordingly, the image processing device 100 detects an event corresponding to a physical act between medicine preparing tools used when persons such as doctors, nurses or pharmacists deal with medicine. Further, description of the same items as in the first example is omitted from this example to clarify the description.

(1) Example of an Object

FIG. 15 is an explanatory diagram for describing one example of object data in the second example. Referring to FIG. 15, object data 142b is represented as one example stored by the object DB 140. The object data 142b includes five data items that are called "Object ID," "Name," "Product Number," "Type" and "Feature Quantity," as represented as the object data 142a in the first example.

In the example of FIG. 15, as names, "Medicine Bottle" is given to an object Obj21, "Spoon" is given to an object Obj22, "Medicine Package" is given to an object Obj23, "Scale" is given to an object Obj24, and "Package" is given to an object Obj25.

For this example, some of the following five types are assigned to each object.

"SOURCE" . . . A type representing the object of the transportation source of substance "TRANSPORTER 1" . . . A type representing an object capable of transporting the substance "TRANSPORTER 2" . . . A type representing an object capable of transporting the substance "SCALE" . . . A type representing an object capable of measuring the substance "DESTINATION" . . . A type representing the object of the transportation destination of the substance In the example of FIG. 15, the type of the object Obj21 is "SOURCE," the type of the object Obj22 is "TRANSPORTER 1," the type of the object Obj23 is "TRANSPORTER 2," the type of the object Obj24 is "SCALE," and the type of the object Obj25 is "DESTINATION."

(2) Event

For this example, the event detection unit 150 detects an event corresponding to a physical act between medicine preparing tools identified by the object identification unit 130. For example, as events in which objects illustrated in FIG. 15 take part, the following events are given.

Event Ev21) Taking medicine out of a medicine bottle with a spoon

Event Ev22) Movement of the medicine from the spoon to a medicine package

Event Ev23) Putting the medicine into a package from the spoon

Event Ev24) Putting the medicine into the package from the medicine package

Event Ev25) Measuring the medicine contained in the medicine package on a scale

These events may be detected under conditions that given event detecting conditions, for example, for two objects, are satisfied. The given event detecting conditions may be some of the following conditions, for example.

Condition C21) The distance between two objects is lower than a threshold value.

Condition C22) One object is placed on another object.

Condition C23) The time for which the condition C21 or the condition C22 has continuously been satisfied is over a threshold value.

Condition C24) A given gesture of a person using two objects is identified.

The distance in the condition C21 may be a 2D distance in an input image or a 3D distance in the actual space recognized based on a known 3D structure recognizing technology. Threshold values for the conditions C21 and C23 may be defined in common without depending on objects or individually for each object.

(3) Control of the Attributes

In this example, if the types defined for objects involved in the detected event satisfy given attribute control conditions, the attribute control unit 170 changes the attributes of those objects. The attribute control conditions are defined in an attribute control table.

Figure 16:
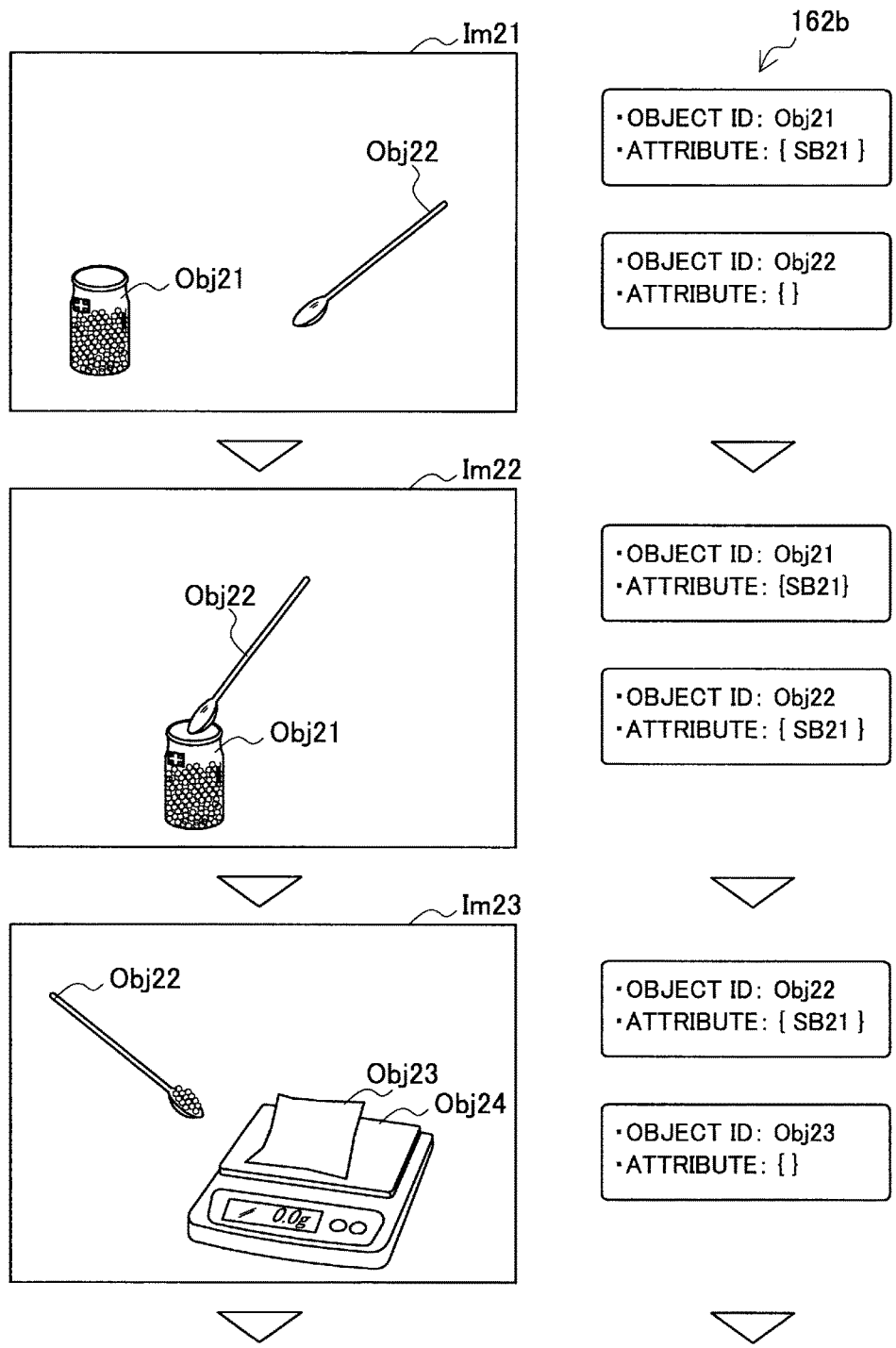
FIG. 16 is an explanatory diagram for describing one example of an attribute control table in a second example.

FIG. 16 is an explanatory diagram for describing one example of an attribute control table in the second example. Referring to FIG. 16, an attribute control table 144b is illustrated as one example stored in the object DB 140. The attribute control table 144b is defined in a matrix form with five types of objects in both columns and rows. Each column corresponds to the type of a first object involved in an event. Each row corresponds to the type of a second object involved in the event.

For example, if the type of the first object is "SOURCE" and the type of the second object is "TRANSPORTER 1" or "TRANSPORTER 2," then an attribute associated with the first object is added to (or newly associated with) the second object. The attribute of the first object are not updated.

In addition, if the type of the first object is "TRANSPORTER 1" and the type of the second object is "TRANSPORTER 2" or "DESTINATION," then an attribute associated with the first object is added to the second object. The attribute of the first object is eliminated.

In addition, if the type of the first object is "TRANSPORTER 2" and the type of the second object is "DESTINATION," then an attribute associated with the first object is added to the second object. The attribute of the first object is eliminated.

In addition, if the type of the first object is "TRANSPORTER 2" and the type of the second object is "SCALE," then the amount of the substance is added to an attribute associated with the second object. In other words, the attribute control unit 170 reads the measurement result by a scale, for example, with the type "SCALE" from an input image (by applying known OCR (Optical Character Recognition) technology to a display panel), and adds the value for the read amount to the attributes of the second object.

Likewise, if the type of the first object is "SCALE" and the type of the second object is "DESTINATION," then the amount of the substance is added to an attribute associated with the first object.

For other types of combinations, the attributes of the first and second objects are not updated.

Further, for a tool, such as a measuring spoon, two types that are called "TRANSPORTER 2" and "SCALE" may be set. In addition, to a tool used for measuring a fixed amount, a value pre-defined for a fixed amount instead of a dynamically read value may be assigned.

(4) Data Transition

Figure 17:
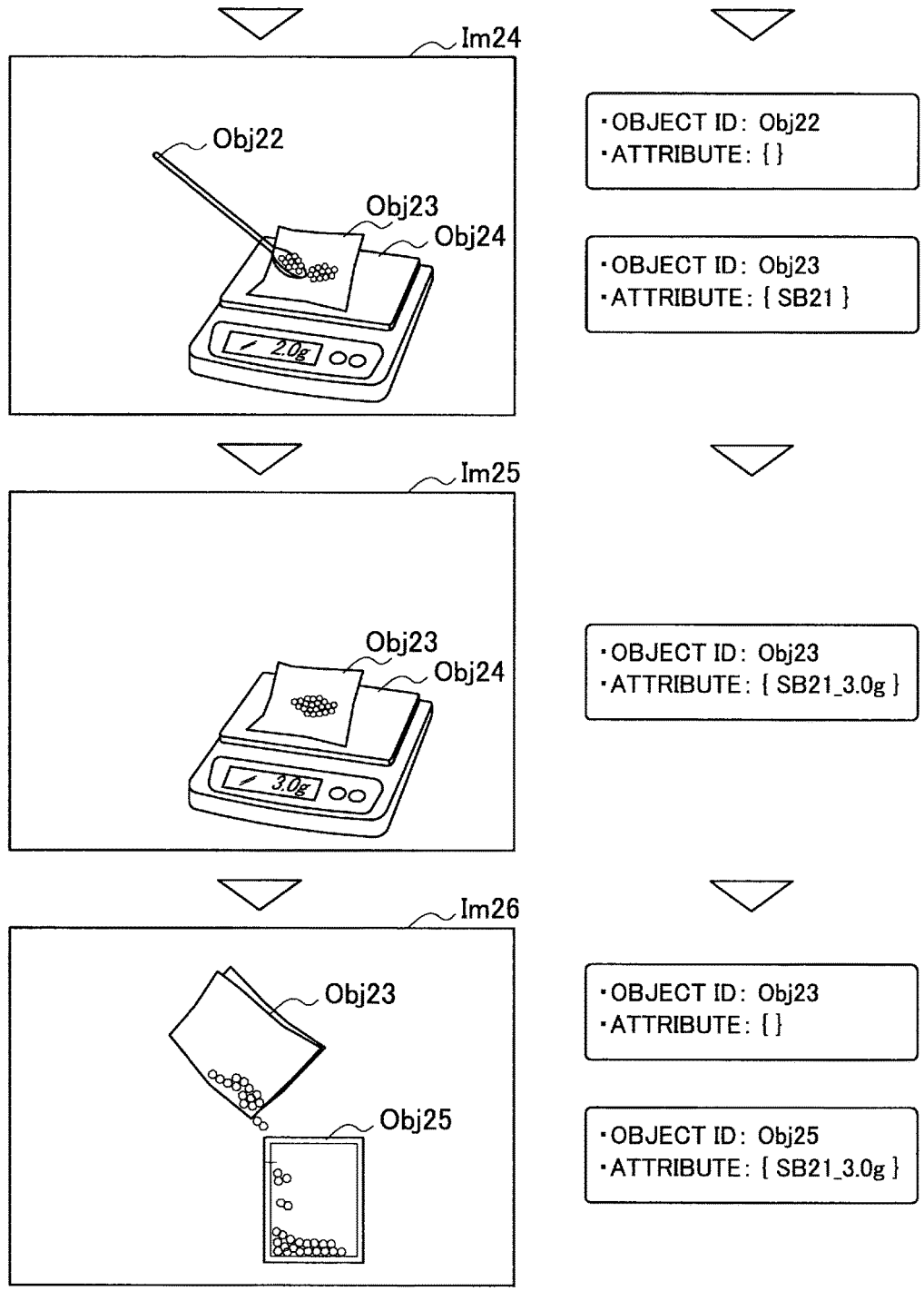
FIG. 17A is a first half of an explanatory diagram for describing one example of the state transition of attribute data in a second example.
FIG. 17B is a second half of an explanatory diagram for describing one example of the state transition of attribute data in a second example.

FIGS. 17A and 17B are explanatory diagrams for describing one example of the state transition of attribute data according to an exemplary scenario in this example. On the left of these drawings, six input images Im21 to Im26 acquired in a time series are sequentially illustrated, and on the right thereof, the partial content of the attribute data 162b at each point in time is illustrated.

Referring to FIG. 17A, in the input image Im21, a medicine bottle Obj21 and a spoon Obj22 appear. For the attribute data 162b, an attribute value representing a substance SB21 is associated with the medicine bottle Obj21. This represents that the substance SB21 is contained in the medicine bottle Obj21. On the other hand, no attribute values are associated with the spoon Obj22. This represents that nothing is contained in the spoon Obj22.

Then, in the input image Im22, the spoon Obj22 appears over the medicine bottle Obj21. The event detection unit 150 detects an event corresponding to the extraction of medicine between the medicine bottle Obj21 and the spoon Obj22, according to, for example, the event detecting condition C22 or C23 described above. According to the object data 142b, the type of the medicine bottle Obj21 is "SOURCE" and the type of the spoon Obj22 is "TRANSPORTER 1." The attribute control unit 170 determines the control content of the attribute corresponding to a combination of "SOURCE" and "TRANSPORTER 1" by referring to the attribute control table 144b, and newly associates the attribute value "SB21" associated with the medicine bottle Obj21, with the spoon Obj22. As a result, the attribute data 162b represents that the substance SB21 is contained in the spoon Obj22.

Then, in the input image Im23, the spoon Obj22, the medicine package Obj23 and the scale Obj24 appear. For the attribute data 162b, an attribute value representing the substance SB21 is associated with the spoon Obj22. On the other hand, no attribute value is associated with the medicine package Obj23.

Then, referring to FIG. 17B, in the input image Im24, the spoon Obj22 appears over the medicine package Obj23. The event detection unit 150 detects an event corresponding to movement of medicine between the spoon Obj22 and the medicine package Obj23, according to, for example, the event detecting condition C22 or C23 described above. According to the object data 142b, the type of the spoon Obj22 is "TRANSPORTER 1" and the type of the medicine package Obj23 is "TRANSPORTER 2." The attribute control unit 170 determines the control content of the attribute corresponding to a combination of "TRANSPORTER 1" and "TRANSPORTER 2" by referring to the attribute control table 144b, and newly associates the attribute value "SB21" associated with the spoon Obj22, with the medicine package Obj23. As a result, the attribute data 162b represents that the substance SB21 is contained in the medicine package Obj23.

Then, in the input image Im25, a figure in which the scale Obj24 measures the amount of the substance contained in the medicine package Obj23 appears. According to the object data 142b, the type of the medicine package Obj23 is "TRANSPORTER 2" and the type of the scale Obj24 is "SCALE." The attribute control unit 170 reads values for the amount displayed by the scale Obj24 from the input image Im25, and adds the read values to the attribute of the medicine package Obj23. In the example of FIG. 17B, the attribute data 162b represents that 3.0 g of the substance SB21 is contained in the medicine package Obj23.

Then, in the input image Im26, the medicine package Obj23 appears over the package Obj25. The event detection unit 150 detects an event corresponding to the putting of medicine into the package Obj25 from the medicine package Obj23. According to the object data 142b, the type of the medicine package Obj23 is "TRANSPORTER 2" and the type of the package Obj25 is "DESTINATION." The attribute control unit 170 determines the control content of the attribute corresponding to a combination of "TRANSPORTER 2" and "DESTINATION" by referring to the attribute control table 144b, and newly associates the attribute value "SB21_3.0g" associated with the medicine package Obj23, with the package Obj25. As a result, the attribute data 162b represents that 3.0 g of the substance SB21 is contained in the package Obj25.

(5) Example of Display

Figure 18:
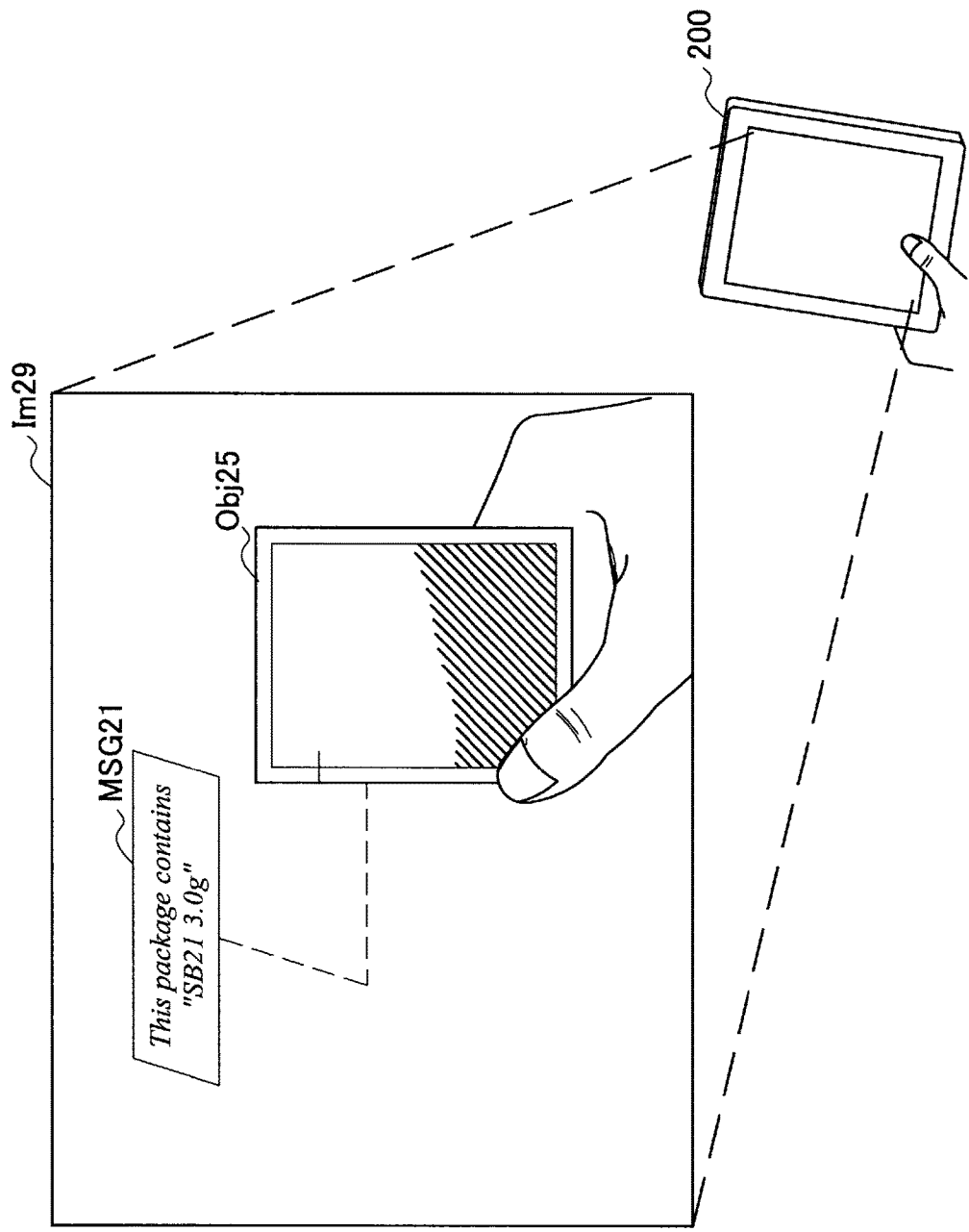
FIG. 18 is an explanatory diagram for describing one example of output images shown for a second example.

FIG. 18 is an explanatory diagram for describing one example of output images displayed by the terminal device 200 for this example. Referring to FIG. 18, an output image Im29 is illustrated as one example. In the output image Im29, the package Obj25 appears. In addition, the output image Im29 is overlapped with a message MSG21 indicating the package Obj25. The message MSG21 represents that the package Obj25 contains 3.0 g of the substance SB21. The user of the terminal device 200 can easily recognize, for example, by reading such a message MSG21, how much of what type of medicine has been contained in the package Obj25.

(6) Flow of Processing

Figure 19:
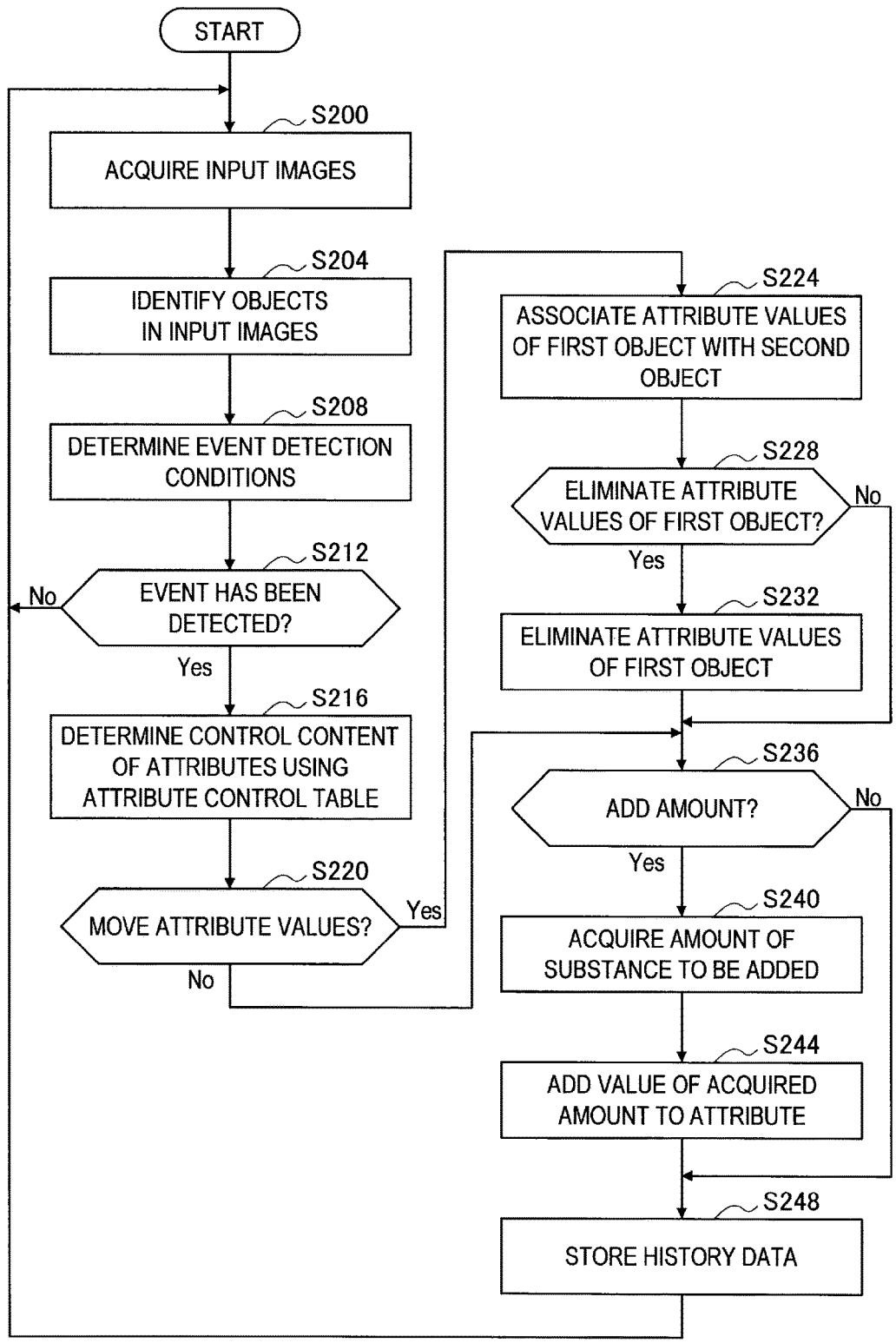
FIG. 19 is a flowchart illustrating one example of the flow of attribute control processing in a second example.

FIG. 19 is a flowchart illustrating one example of the flow of attribute control processing by the image processing device 100 in this example. The attribute control processing shown in FIG. 19 is repeated for input images sequentially acquired by the image acquisition unit 120.

First, the image acquisition unit 120 acquires captured images generated by the imaging unit 102 as input images (step S200). In addition, the image acquisition unit 120 outputs the acquired input images to the object identification unit 130.

Then, the object identification unit 130 identifies objects in the input images with known feature quantities of each object stored by the object DB 140 (step S204).

Then, the event detection unit 150 determines whether the event detecting conditions described above for the objects identified by the object identification unit 130 are satisfied (step S208). At this point, if the event detecting conditions are not satisfied, the following processing is skipped (step S112). If the event detecting conditions are satisfied, the event detection unit 150 notifies the attribute control unit 170 of the detected event.

If the event is detected by the event detection unit 150, the attribute control unit 170 determines the control content of the attributes of objects involved in the detected event using the attribute control data 144b (step S216). In addition, if it is determined to move an attribute value from a first object to a second object (step S220), then the attribute control unit 170 associates the attribute value associated with the first object, with the second object (step S224). In addition, if it is determined to eliminate the attribute value of the first object (step S228), then the attribute control unit 170 eliminates the attribute value associated with the first object (step S232).

In addition, if it has been determined to increase the amount of any object (step S239), then the attribute control unit 170 acquires values for the amount of a substance to be added (step S240) and adds the acquired values to the attribute of any object excluding the object "SCALE" (step S244).

In addition, the attribute control unit 170 stores new records of history data 164 including the attribute values before and after being updated in the attribute DB 160 (step S248). Further, if no attributes of any object are updated, the processing of S248 is skipped.

So far, a second example has been described with FIGS. 15 to 19. According to this example, in a state in which medicine is combined using a medicine preparing tool, it is possible to recognize the ingredients of the medicine contained in the medicine preparing tool through the attributes of an object. In addition, it is possible to add the amount of the substance contained in the object to the attributes of the object. In addition, persons other than the operator can also easily recognize the ingredients and the amount of the medicine by reading an update history of the attributes or the attribute data of an object. When the attributes of the object are updated, there is no need for a preparer of the medicine to input data.

6. Third Example

In the third example, ingestion of medicine by a patient is illustrated as the target of history management. Accordingly, the image processing device 100 detects an event corresponding to a physical act between the patient and the medicine, an action of ingesting the medicine. Further, description of the same items with any preceding example is omitted from this example to clarify the description.

(1) Example of an Object

FIG. 20 is an explanatory diagram for describing one example of object data in the third example. Referring to FIG. 20, object data 142c is illustrated as one example stored by the object DB 140. The object data 142c includes person data regarding person objects and prescription medicine data regarding prescription medicine objects.

The person data includes three data items that are called "Object ID," "Name," and "Feature Quantity." "Object ID" is an identifier for immediately identifying each person object. "Name" represents each person's name. "Feature Quantity" is extracted from a known face image of each person.

The prescription medicine data includes five data items that are called "Object ID," "Name," "Patient ID," "Dosage" and "Feature Quantity." "Object ID" is an identifier for immediately identifying each prescription medicine object. "Name" represents the name of each prescription medicine. "Patient ID" represents the object ID of a person ingesting each prescription medicine. In FIG. 20, a person ingesting an object Obj35, that is, "X1 Tablet" is an object Obj31, that is, "Mr./Ms. XX." "Dosage" represents information how much prescription medicine a patient should ingest. "Feature Quantity" is extracted from a known image of each prescription medicine.

(2) Event

For this example, the event detection unit 150 detects an event corresponding to an action of ingesting prescription medicine by a person identified by the object identification unit 130. The event detection unit 150 may detect a gesture of ingesting medicine by the person, for example, using known gesture identifying technology. An event detecting condition in this example is as follows.

Condition C31) A gesture of a person object ingesting a prescription medicine object is recognized.

(3) Control of Attributes

If an event corresponding to an action of ingesting medicine is detected by the event detection unit 150, then the attribute control unit 170 updates the attributes of the person object involved in action of ingesting medicine and the prescription medicine object. For example, the attribute control unit 170 may newly associate the attributes representing the dosage and the kind of substance contained in the prescription medicine object, with the person object. In addition, the attribute control unit 170 may eliminate an amount corresponding to the dosage from the attributes of the prescription medicine object. Further, when the attributes of the object is updated, the attribute control unit 170 stores records representing an updated history in the history data 164c.

FIG. 21 represents the content of history data 164c as one example generated by the attribute control unit 170 in this example. Referring to FIG. 21, the history data 164c includes three data items that are called "Object ID," "Attribute" and "Time." "Object ID" is an identifier identifying the person object representing the person ingesting the prescription medicine. "Attribute" represents an attribute value newly associated with the person object by the attribute control unit 170. "Time" represents the detected time of a corresponding event (or may be the updated time of an attribute). The attribute control unit 170 acquires time authenticating data corresponding to these times from an external time authenticating server to enhance the reliability of the history, and may store the acquired time authenticating data by associating the obtained time authenticating data with the history as shown in FIG. 21. In the example of FIG. 21, at the times T31, T32 and T33, the history data 164c shows that the patient Obj31 has ingested two tablets of the substance 31 each time.

Further, in response to the detection of an event corresponding to an action of ingesting medicine, the attribute control unit 170 may transmit a notice message to a terminal device, which a corresponding doctor, a nurse or a patient's family have. In addition, the attribute control unit 170 may transmit an alarm message or emit an alarm if it has been detected that a patient has ingested medicine that the patient should not have ingested.

(4) Data Transition

Figure 22:
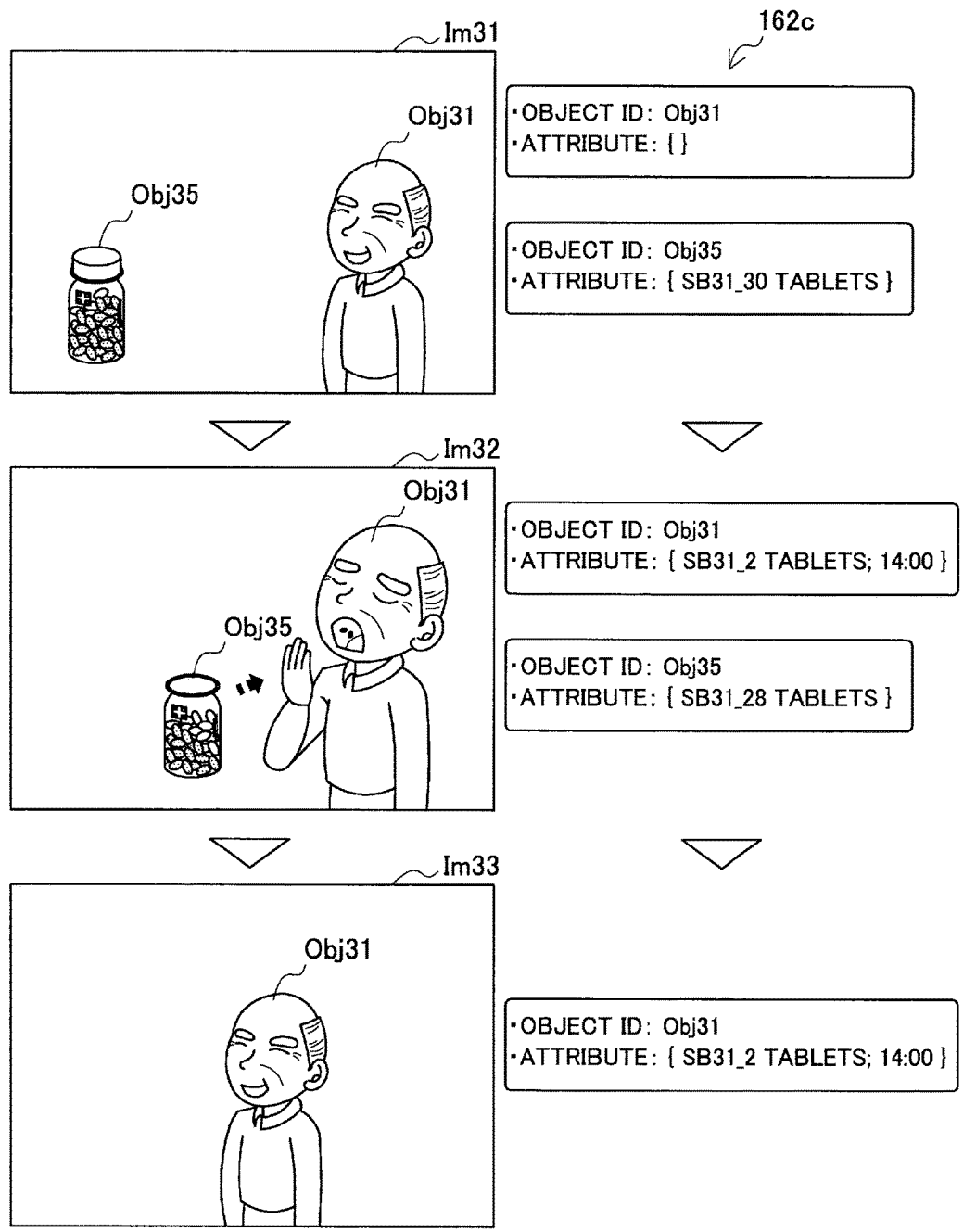
FIG. 22 is an explanatory diagram for describing one example of the state transition of attribute data in a third example.

FIG. 22 is an explanatory diagram for describing one example of the state transition of attribute data according to an exemplary scenario in this example. On the left of the drawing, three input images Im31 to Im33 acquired in a time series are sequentially illustrated, and on the right thereof, the partial content of the attribute data 162c at each point in time is illustrated.

Referring to FIG. 22, in the input image Im31, a patient Obj31 and a prescription medicine Obj35 appear. For attribute data 162c, no attribute value is associated with the patient Obj31. On the other hand, an attribute value representing the kind and amount 30 tablets of the substance SB31 is associated with the prescription medicine Obj35. This represents that 30 tablets of the substance SB31 are contained in the prescription medicine Obj35.

Next, in the input image Im32, a figure in which the patient Obj31 ingests a prescription medicine Obj35 appears. By recognizing a gesture of such an action of ingesting medicine, the event detection unit 150 detects an event corresponding to the action of ingesting the medicine. Then, the attribute control unit 170 newly associates the attribute value "SB31" associated with the prescription medicine Obj35, with the patient Obj31. In addition, the attribute control unit 170 adds the amount corresponding to the dosage to the attribute of the patient Obj31. In addition, the attribute control unit 170 eliminates the amount corresponding to the dosage from the attribute of the prescription medicine Obj35. As a result, the attribute data 162c represents that the patient Obj31 ingested 2 tablets of the substance 31, and 28 tablets of the substance 31 are contained in the prescription medicine Obj35.

Next, a patient Obj31 appears in an input image Im33. The attribute data 162c represents that the patient Obj31 continuously ingested two tablets of the substance 31. Further, the attribute control unit 170 may eliminate attributes associated with the patient object when the event has been detected, after the sustain time of the effect of the prescription medicine passed from the detected time of the event corresponding to the ingestion action.

(5) Example of Display

Figure 23:
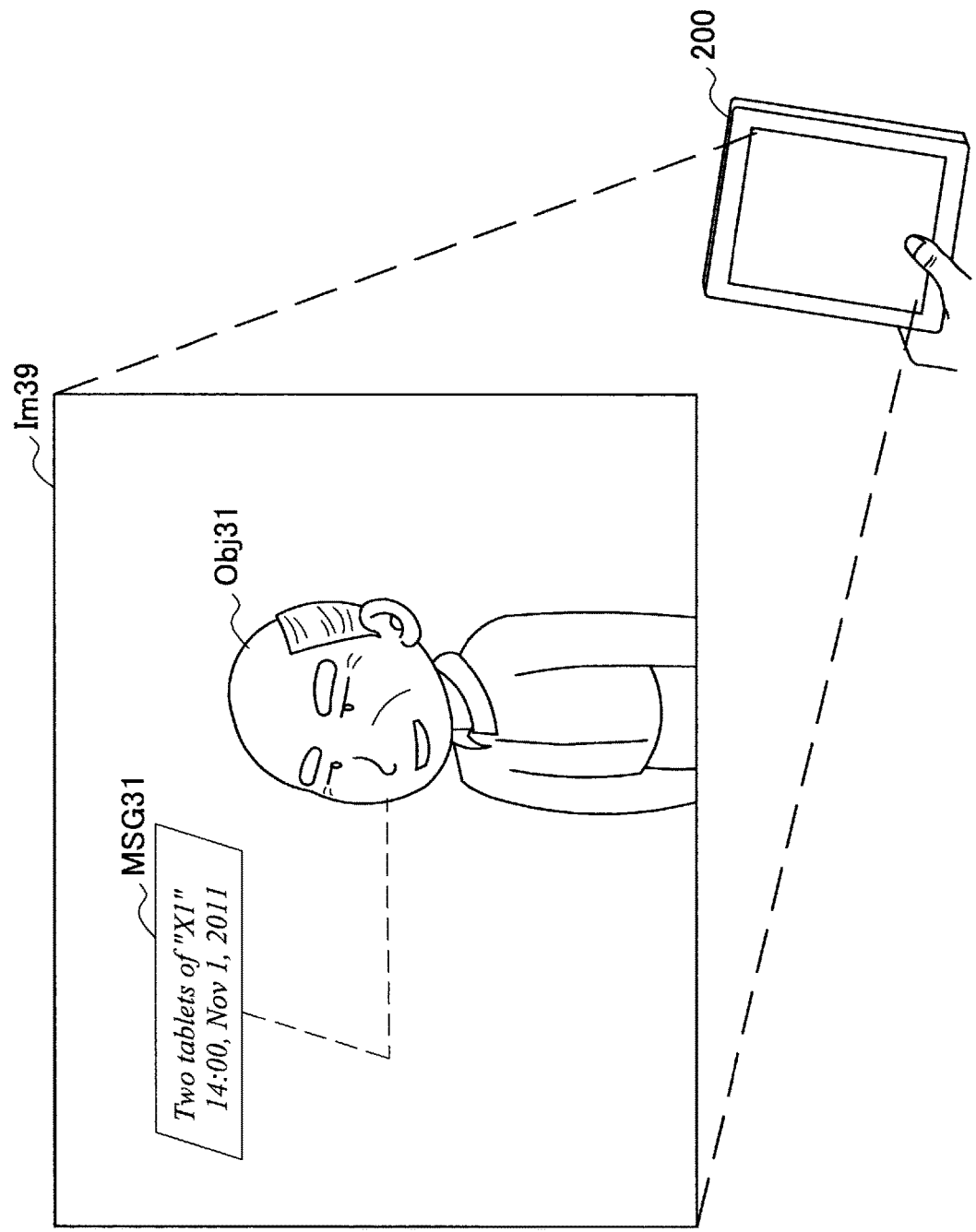
FIG. 23 is an explanatory diagram for describing one example of output images shown for a third example.

FIG. 23 is an explanatory diagram for describing one example of output images displayed by the terminal device 200 for this example. Referring to FIG. 23, an output image Im39 is represented as one example. In the output image Im39, the patient Obj31 appears. In addition, the output image Im39 is overlapped with a message MSG31 indicating the patient Obj31. The message MSG31 represents that the patient Obj31 ingested two tablets of "X1" at 14:00, on 1 Nov. 2011. The user of the terminal device 200 can easily recognize, for example, by reading such a message MSG31, whether the patient ingested the proper prescription medicine at the proper time.

Further, the user interface unit 190 of the image processing device 100 or the user interface unit 250 of the terminal device 200 causes the object ID or name of a patient to designate a user (e.g. a doctor, a nurse or family), and may provide a UI screen to present the history of the action of ingesting the medicine associated with the designated patient to the user.

(6) Flow of Processing

Figure 24:
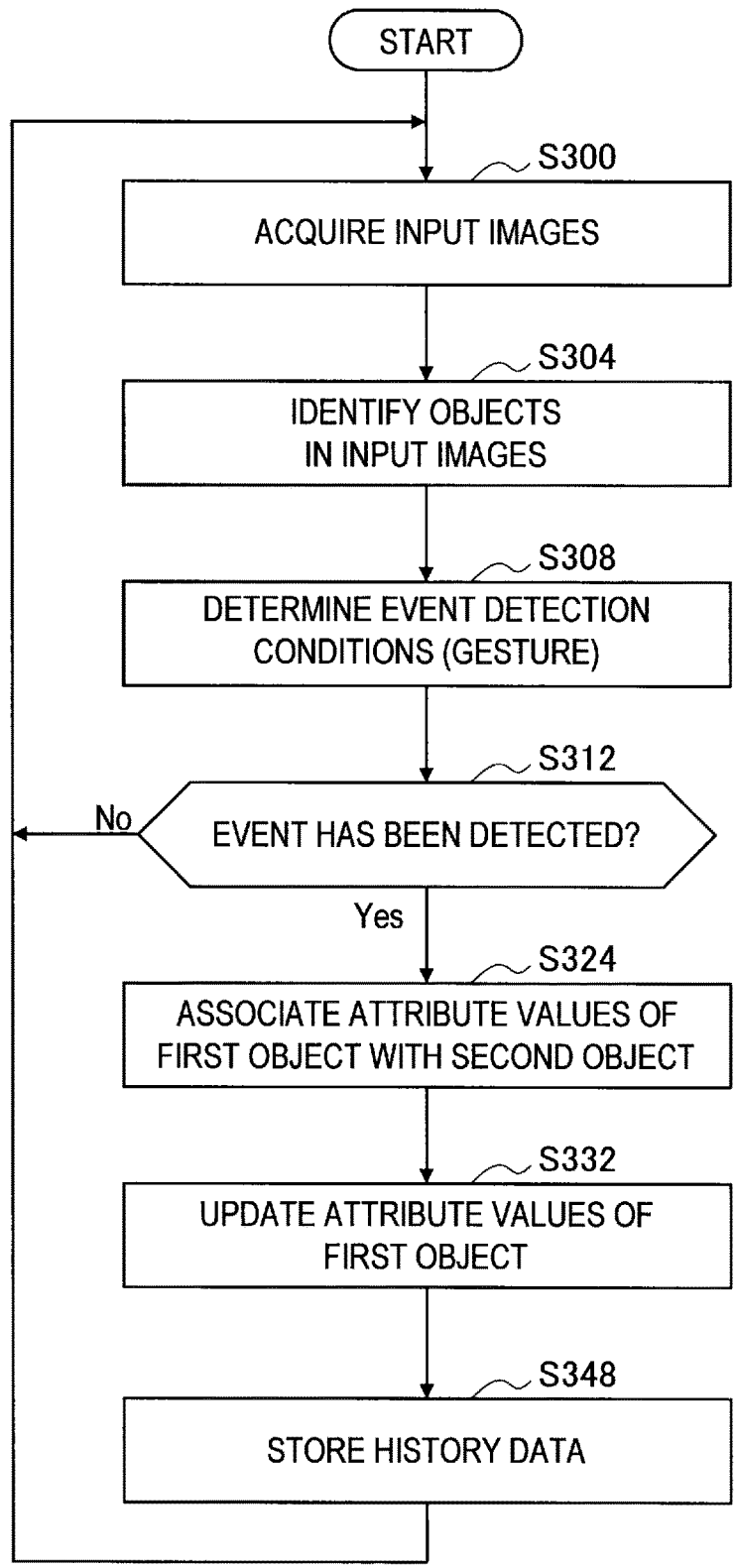
FIG. 24 is a flowchart illustrating one example of the flow of attribute control processing in a third example.

FIG. 24 is a flowchart illustrating one example of the flow of attribute control processing by the image processing device 100 in this example. The attribute control processing shown in FIG. 24 is repeated for input images sequentially acquired by the image acquisition unit 120.

First, the image acquisition unit 120 acquires captured images generated by the imaging unit 102 as input images (step S300). In addition, the image acquisition unit 120 outputs the acquired input images to the object identification unit 130.

Then, the object identification unit 130 identifies these objects in the input images with known feature quantities of a person object and a prescription medicine object stored by the object DB 140 (step S304).

Then, the event detection unit 150 determines whether the event detecting conditions are satisfied using the gesture recognizing technology for the objects identified by the object identification unit 130 (step S308). At this point, if the event detecting conditions are not satisfied, the following processing is skipped (step S312). If the event detecting conditions are satisfied, the event detection unit 150 notifies the attribute control unit 170 of the detected event.

If the event is detected by the event detection unit 150, the attribute control unit 170 associates a dosage and an attribute value associated with a first object, that is, prescription medicine object, with a second object or person object (step S324). In addition, the attribute control unit 170 eliminates the dosage from the amount of attributes associated with the first object (step S332). The attribute control unit 170 stores new records of the history data 164c in the attribute BD 160 (S348).

The third example has been described above with reference to FIGS. 20 to 24. According to this example, in a situation in which a patient ingests prescription medicine, it is possible for a third party to recognize through the updated history of the attributes or the attribute data of an object what type of medicine the patient has ingested and at what time. When the attributes of the object are updated, there is no need for the patient or the third party to input data.

7. Fourth Example

In the fourth example, mixing of food materials and seasonings in food processing actions is illustrated as the target of history management. Accordingly, the image processing device 100 detects an event corresponding to a physical act when chefs, employees of restaurants or employees of food processing factories, etc. use food materials and seasonings. Further, description of the same items as in any preceding example is omitted from this example to clarify the description.

(1) Example of an Object

FIG. 25 is an explanatory diagram for describing one example of object data in the fourth example is described. Referring to FIG. 25, object data 142d is illustrated as one example stored by the object DB 140. The object data 142d includes five data items that are called "Object ID," "Name," "Product Number," "Type" and "Feature Quantity," like the object data 142a in the first example.

For this example, some of the following four types of candidates are assigned to each object.

"SOURCE" A type representing the objects of the transport sources of food materials or seasonings. This can correspond to containers for food materials or seasonings, or food materials themselves "TRANSPORTER 1" A type representing an object capable of transporting the food materials or seasoning "CONTAINER" A type representing an object capable of containing food to be cooked "FOOD_ITEM" A type representing the object of the food to be cooked In the example of FIG. 25, the types of an object Obj41 (minced meat) and an object Obj42 (a black pepper bottle) are "SOURCE." The type of an object Obj43 (a ladle) is "TRANSPORTER." The types of an object Obj44 (a bowl), an object Obj45 (a frying pan) and an object Obj46 (a tray) are "CONTAINER." The type of an object Obj50 (food) is "FOOD_ITEM."

Further, the feature quantity (e.g. feature quantity FD 50 in the object data 142d) for identifying the object "FOOD_ITEM" is not given in an initial state to identify the object "FOOD_ITEM." The feature quantity of the object "FOOD_ITEM" can be extracted from an input image in response to the detection of an event, which will be described later.

(2) Event

For this example, the event detection unit 150 detects an event corresponding to a physical act between objects identified by the object identification unit 130. For example, as events in which objects illustrated in FIG. 25 take part, the following events are given.

Event Ev41) Putting minced meat into a bowl

Event Ev42) Putting black pepper from the black pepper bottle into the bowl

Event Ev43) Movement of food from the bowl to the frying pan

Event Ev44) Movement of the food from the frying pan to the tray

These events may be detected under conditions that given event detecting conditions, for example, for two objects, are satisfied. The given event detecting conditions may be some of the following conditions, for example.

Condition C41) One object is placed on another object.

Condition C42) The time for which the condition C41 has been continuously satisfied is over a threshold value.

Condition C43) A given gesture of a person using two objects is identified.

The threshold value for the condition C42 may be defined in common without depending on objects or individually for each object.

(3) Control of the Attributes

In this example, if the types defined for objects involved in a detected event satisfy given attribute control conditions, the attribute control unit 170 updates the attributes of those objects. The attribute control conditions are defined in an attribute control table.

FIG. 26 is an explanatory diagram for describing one example of an attribute control table in the fourth example. Referring to FIG. 26, an attribute control table 144d is illustrated as one example stored in the object DB 140. The attribute control table 144d is defined in a matrix form with four types of objects in both columns and rows. Each column corresponds to the type of a first object involved in an event. Each row corresponds to the type of a second object involved in the event.

For example, if the type of the first object is "SOURCE" and the type of the second object is "TRANSPORTER," then an attribute associated with the first object is added to (or newly associated with) the second object. The attribute of the first object is not updated.

If the type of the first object is "SOURCE" and the type of the second object is "CONTAINER," then it is determined whether there is a third object contained in the second object, and if not, that third object is generated. The third object generated at this point is the object "FOOD_ITEM." In addition, an attribute associated with the first object is added to the third object. Further, new feature quantities of the third object are extracted from input images. The attribute of the first object is not updated.

In addition, if the type of the first object is "SOURCE" and the type of the second object is "FOOD_ITEM," then an attribute associated with the first object is added to the second object. Further, new feature quantities of the third object are extracted from input images. The attribute of the first object is not updated.

In addition, if the type of the first object is "TRANSPORTER" and the type of the second object is "CONTAINER," then it is determined whether there is a third object contained in the second object, and if not, that third object is generated. The third object generated at this point is the object "FOOD_ITEM." In addition, an attribute associated with the first object is added to the third object. Further, new feature quantities of the third object are extracted from input images. The attribute of the first object is eliminated.

In addition, if the type of the first object is "TRANSPORTER" and the type of the second object is "FOOD_ITEM," then an attribute associated with the first object is added to the second object. Further, new feature quantities of the second object are extracted from input images. The attribute of the first object is eliminated.

In addition, if the type of the first object is "CONTAINER" and the type of the second object is also "CONTAINER," then an attribute associated with the first object is added to the second object. Further, new feature quantities of the second object are extracted from input images. The attribute of the first object is eliminated.

In addition, if the type of the first object is "CONTAINER" and the type of the second object is "FOOD_ITEM," then an attribute associated with the first object is added to the second object. Further, new feature quantities of the second object are extracted from input images. The attribute of the first object is eliminated.

For other types of combinations, the attributes of the first and second objects are not updated.

Further, feature quantities of the object "FOOD_ITEM" may be extracted from a differential area that is determined by excluding a part of a known object "CONTAINER" from the image area of the object "CONTAINER" containing the object "FOOD_ITEM." When an event in which the object "FOOD_ITEM" takes part has been detected and no great change in the appearance of the object occurs, the attribute control unit 170 may neither extract nor update feature quantities of that object. In addition, also in this example, the type "SCALE" representing an object capable of measuring a substance may be further used, as described in the second example.

(4) Data Transition

Figure 27A:
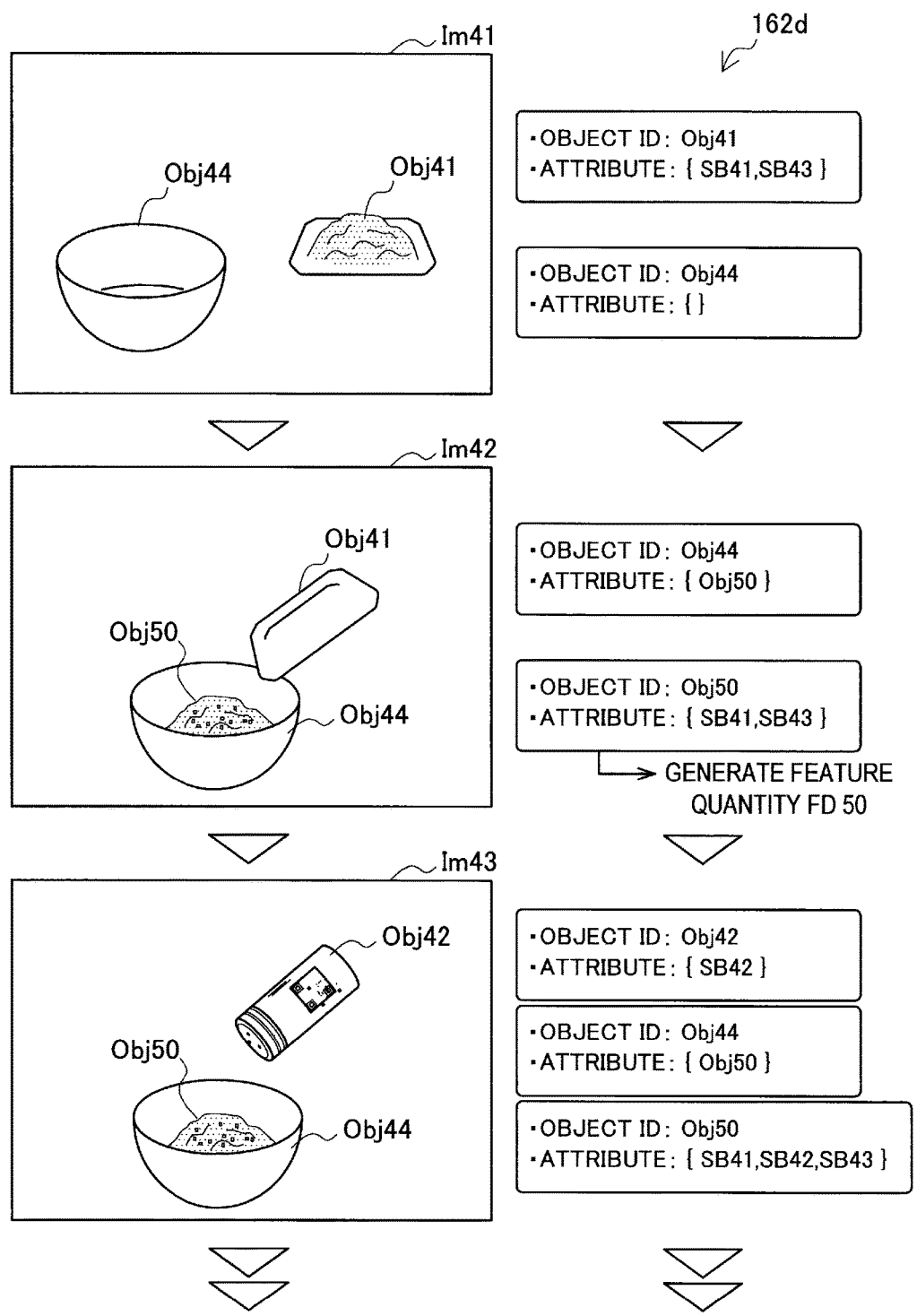
FIG. 27A is a first half of an explanatory diagram for describing one example of the state transition of attribute data in a fourth example.
Figure 27B:
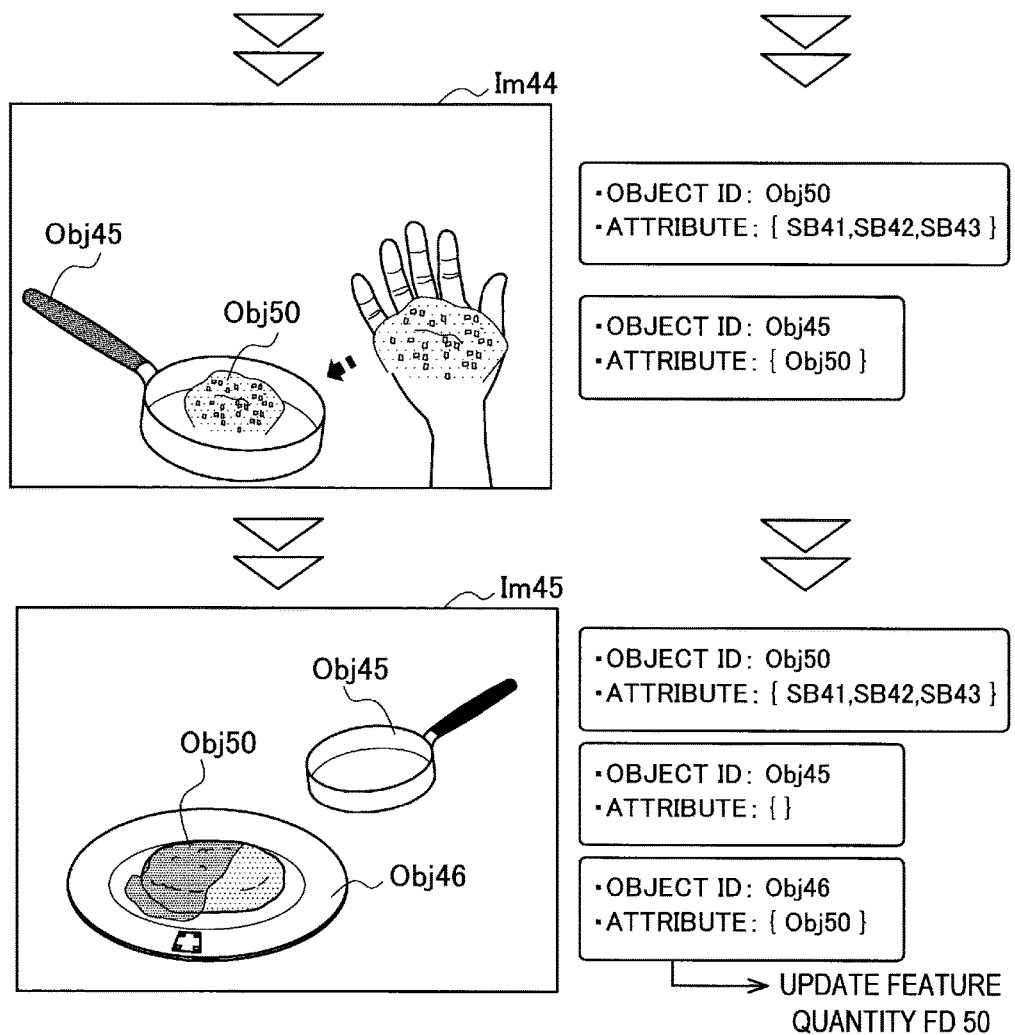
FIG. 27B is a second half of an explanatory diagram for describing one example of the state transition of attribute data in a fourth example.

FIGS. 27A and 27B are explanation diagrams for describing one example of the state transition of attribute data according to an exemplary scenario in this example. On the left of these drawings, five input images Im41 to Im45 acquired in a time series are sequentially illustrated, and on the right thereof, the partial content of the attribute data 162d at each point in time is illustrated.

Referring to FIG. 27A, in the input image Im41, minced meat Obj41 and a bowl Obj44 appear. For the attribute data 162d, with the minced meat Obj41, attribute values representing a substance SB41 and a substance SB43 are associated. This represents that the minced meat Obj41 has the substance SB41 and the substance SB43 as its constitutional components. On the other hand, no attribute value is associated with the bowl Obj44. This represents that nothing is contained in the bowl Obj44.

Then, for the input image Im42, the minced meat Obj41 appears over the bowl Obj44. The event detection unit 150 detects an event corresponding to putting the minced meat Obj41 into the bowl Obj44, according to, for example, any of the event detecting conditions C41 to C43 described above. According to the object data 142d, the type of the minced meat Obj41 is "SOURCE" and the type of the bowl Obj44 is "CONTAINER." The attribute control unit 170 newly generates food Obj50, the object "FOOD_ITEM," according to control content shown by the attribute control table 144d, and associates the attribute values "SB41" and "SB43" associated with the minced meat Obj41, with the food Obj50. The attribute value representing the food Obj50 is associated with the bowl 44. Further, the attribute control unit 170 extracts the feature quantity FD 50 of the food Obj50 from the input image Im42, and stores the extracted feature quantity FD 50 in the object DB 140.

Then, in the input image Im43, the black pepper bottle Obj42, the bowl Obj44 and the food Obj50 appear. The event detection unit 150 detects an event corresponding to putting black pepper into the food Obj50 in the bowl Obj44, according to, for example, any of the event detecting conditions C41 to C43 described above. At this point, the type of the food Obj50 is "FOOD_ITEM" and the type of the black pepper bottle Obj42 is "SOURCE." The attribute control unit 170 newly associates the attribute value "SB42" associated with the black pepper bottle Obj42, with the food Obj50 according to control content shown by the attribute control table 144d. For the attribute data 162d, an attribute value representing the substance SB42 (black pepper) is associated with the black pepper bottle Obj42. An attribute value representing the food Obj50 is associated with the bowl Obj44. Attribute values representing the substances SB41, SB42 and SB43 are associated with the food Obj50.

Next, referring to FIG. 27B, in the input image Im44, a figure in which the food Obj50 is contained in the frying pan Obj45 appears. The attribute data 162d represents that the food Obj50 is contained in the frying pan Obj45, and the food Obj50 has the substances SB41, SB42 and SB43 as constitutional components.

Further, after finishing cooking in the frying pan Obj45, in the input image Im45, the tray Obj46 appears near the frying pan Obj45. The event detection unit 150 detects an event corresponding to movement of the food Obj50 from the frying pan Obj45 to the tray Obj46. At this point, the types of the frying pan Obj45 and the tray Obj46 are both "CONTAINER." The attribute control unit 70 newly associates the attribute value "Obj50" associated with the frying pan Obj45, with the tray Obj46 according to control content shown by the attribute control table 144*d*. As a result, the attribute data 162*d* represents that the food Obj50 is contained in the tray Obj46. Further, the attribute control unit 170 extracts the feature quantity FD 50 of the food Obj50 from the input image Im42, and stores the extracted feature quantity FD 50 in the object DB 140. At this point, the stored feature quantity FD 50 represents characteristics of the appearance of the food Obj50 cooked using the frying pan Obj45.

(5) Example of Display

Figure 28:
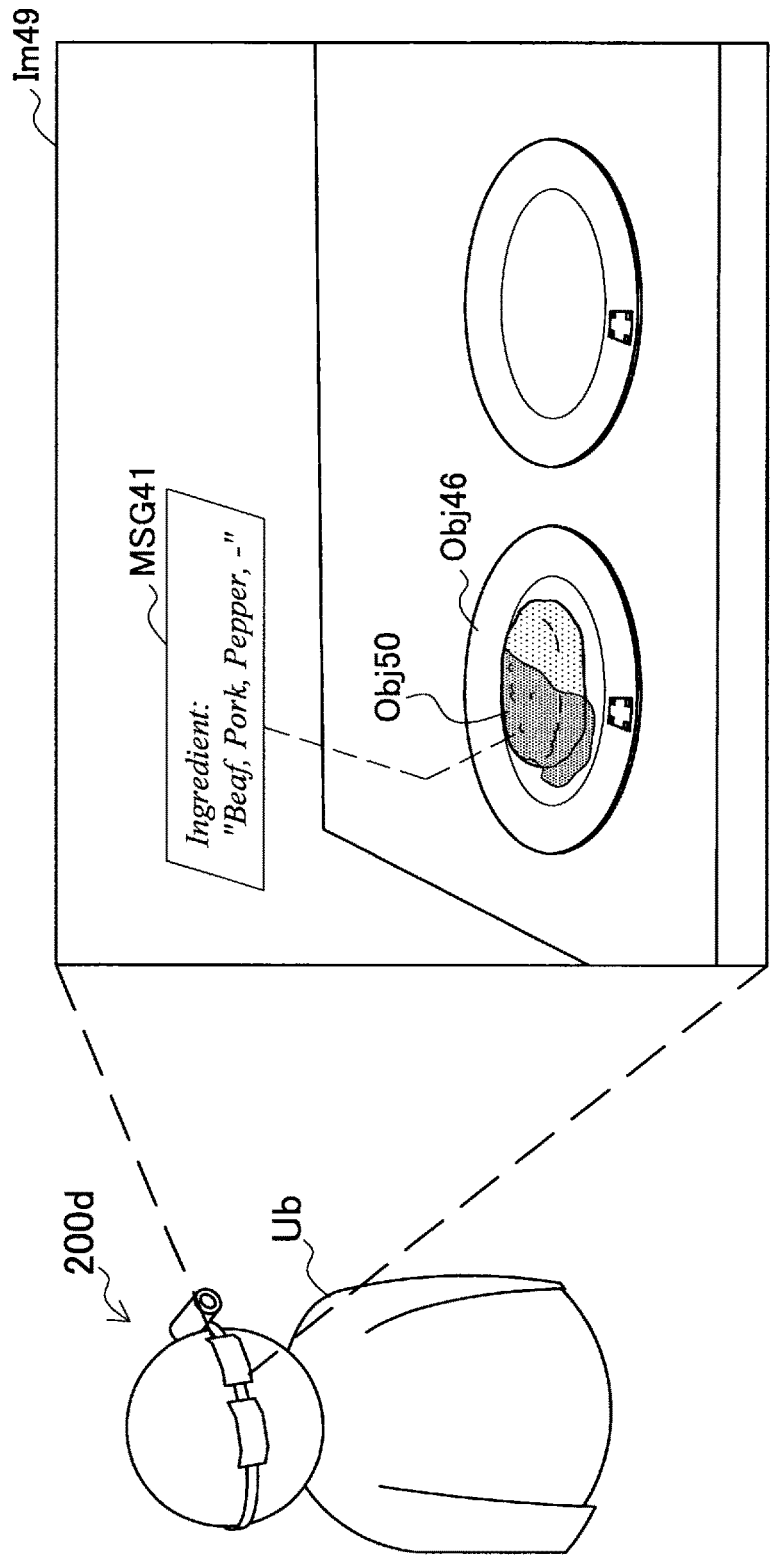
FIG. 28 is an explanatory diagram for describing one example of output images shown for a fourth example.

FIG. 28 is an explanatory diagram for describing one example of output images displayed by the terminal device 200 for this example. Referring to FIG. 28, an output image Im49 is illustrated as one example. In the output image Im49, the tray Obj46 and the food Obj50 appear. In addition, the output image Im49 is overlapped with a message MSG41 indicating the food Obj50. The message MSG41 represents that the food Obj50 includes beef, pork and black pepper, which can correspond to the substances SB41, SB43 and SB42, respectively. The user of the terminal device 200 can easily recognize, for example, by reading such a message MSG41, what components are included in the food Obj50.

(6) Flow of Processing

Figure 29:
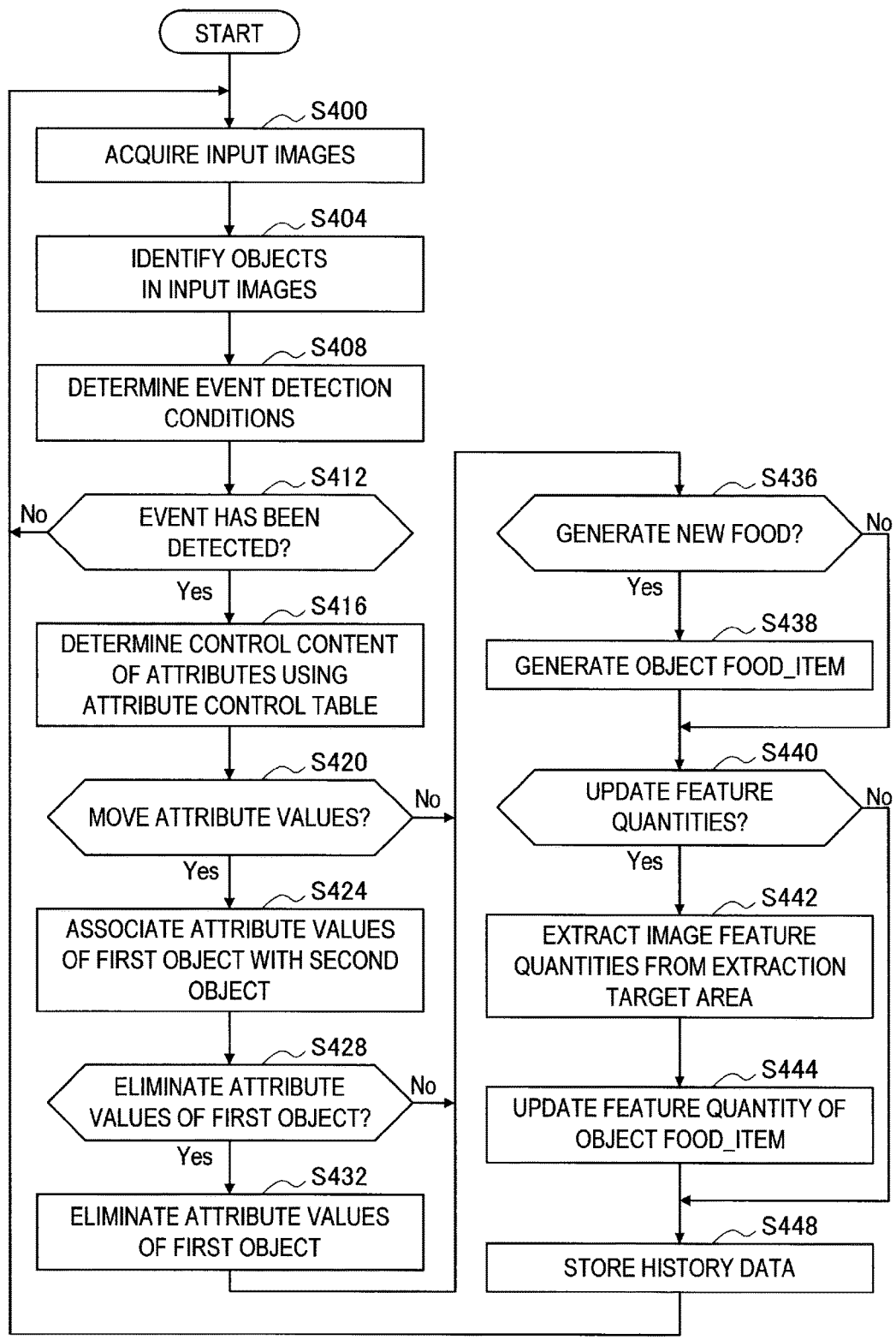
FIG. 29 is a flowchart illustrating one example of the flow of attribute control processing in a fourth example.

FIG. 29 is a flowchart illustrating one example of the flow of attribute control processing by the image processing device 100 in this example. The attribute control processing shown in FIG. 29 is repeated for input images sequentially acquired by the image acquisition unit 120.

First, the image acquisition unit 120 acquires captured images generated by the imaging unit 102 as input images (step S400). In addition, the image acquisition unit 120 outputs the acquired input images to the object identification unit 130.

Then, the object identification unit 130 identifies objects in the input images with known feature quantities of each object stored by the object DB 140 (step S404).

Then, the event detection unit 150 determines whether the event detecting conditions described above for the objects identified by the object identification unit 130 are satisfied (step S408). At this point, if the event detecting conditions are not satisfied, the following processing is skipped (step S412). If the event detecting conditions are satisfied, the event detection unit 150 notifies the attribute control unit 170 of the detected event.

If the event is detected by the event detection unit 150, the attribute control unit 170 determines the control content of the attributes of objects involved in the detected event using the attribute control table 144*d* (step S416). In addition, if it is determined to move an attribute value from a first object to a second object (step S420), then the attribute control unit 170 associates the attribute value associated with the first object, with the second object (step S424). In addition, if it is determined to eliminate the attribute value of the first object (step S428), then the attribute control unit 170 eliminates the attribute value associated with the first object (step S432).

In addition, if it has been determined to generate a new object "FOOD_ITEM" (step S436), then the attribute control unit 170 generates the object "FOOD_ITEM" (step S438). At this point, an attribute value associated with the first object is associated with the generated object "FOOD_ITEM."

In addition, if it has been determined to update feature quantities of the object "FOOD_ITEM" (step S440), then the attribute control unit 170 extracts image feature quantities from an extraction target area described above, and updates feature quantities of the object "FOOD_ITEM" with the extracted image feature quantities (step S444).

In addition, the attribute control unit 170 stores new records of the history data 164 in the attribute DB 160 (step S448). Further, if no attributes of any object can be updated, S448 is skipped.

The fourth example has been described above with reference to FIGS. 25 to 29. According to this example, in a situation in which food is cooked using cooking tools, it is possible to recognize the ingredients of the food through the attributes of an object. Consumers can purchase or eat food without anxiety, because they can easily recognize the ingredients of the processed food by holding a terminal device with a camera over the food.

8. Variation

In the embodiments above, descriptions have been mainly made of examples in which the image processing device 100 and the terminal device 200 are made as physically separate devices. However, the image processing device 100 and the terminal device 200 may be made as an integrated device, as shown in an image processing device 300 illustrated in FIG. 30.

Figure 30:
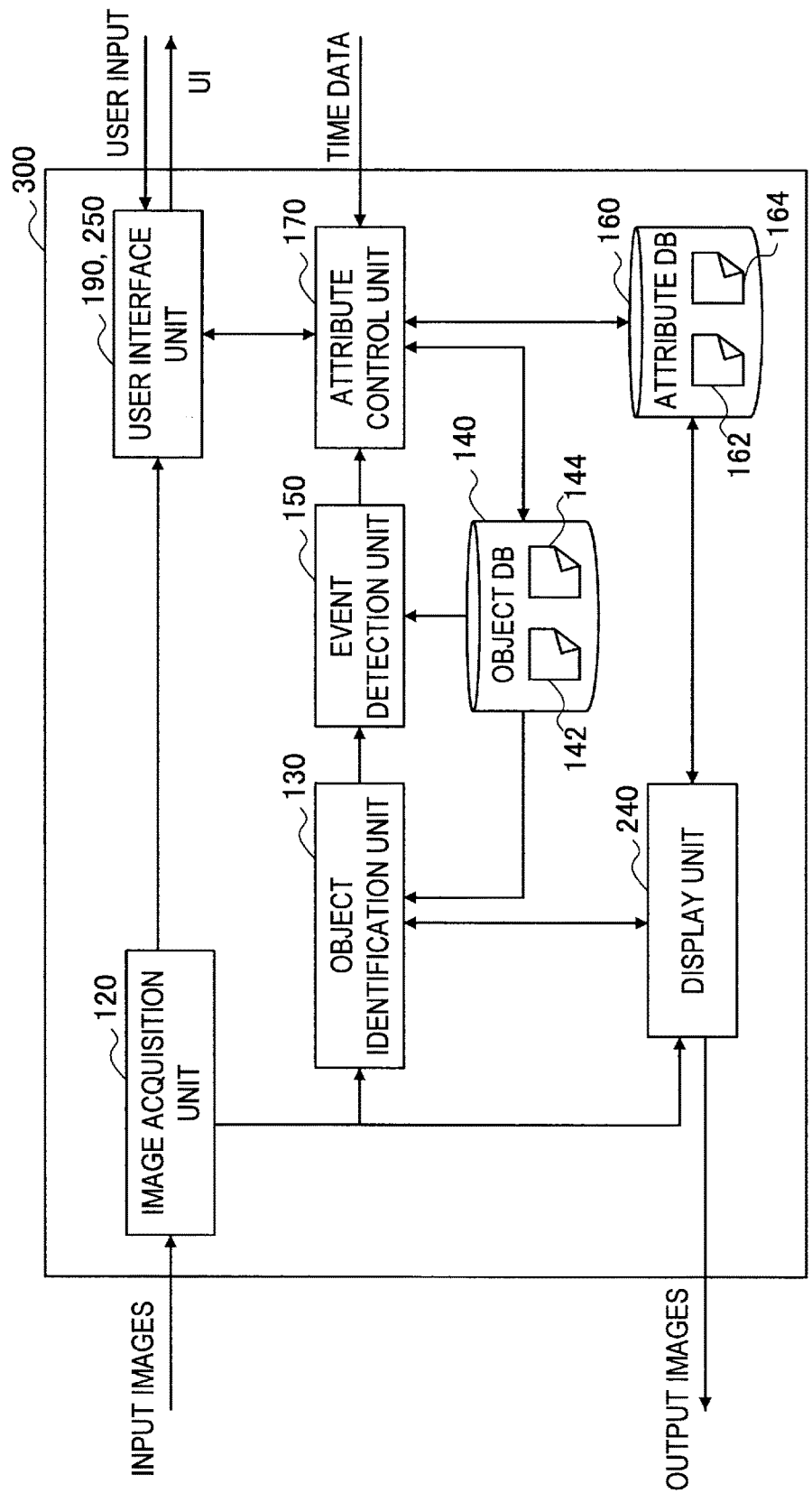
FIG. 30 is a block diagram illustrating one example of a logical functional configuration of an image processing device according to one variation.

FIG. 30 is a block diagram in which one example of the logical functional configuration of the image processing device 300 according to one variation is illustrated. Referring to FIG. 30, the image processing device 300 includes an image acquisition unit 120, an object identification unit 130, an object DB 140, an event detection unit 150, an attribute DB 160, an attribute control unit 170, a display control unit 240 and a user interface unit 190 and 250. The function of each processing block of the image processing device 300, in principle, is the same to that of a processing block with the same reference numeral described above. The display control unit 240 of the image processing device 300 acquires attribute data associated with an object in an input image, from the attribute DB 160, and overlaps the acquired attribute data on the input image.

9. Summary

So far, technology according to an embodiment of the disclosure has been described based on one embodiment and four examples thereof. According to the technology according to an example of the disclosure, objects present in an actual space are identified from an input image, and attribute data associated with a first object is associated with a second object in response to the detection of an event corresponding to a physical act between the identified objects. Accordingly, it is possible to manage a history of various actions resulting in a physical act between these objects, in a format referred to as attributes of objects. Here, the update of the attribute data does not put pressure on an operator, because such update is automatically performed using image recognizing technology.

According to the embodiment, the object may be one capable of containing a substance, and the attribute data can represent the kind of substance contained in an object associated with the attribute data. According to such a configuration, it is possible to later recognize the details of an action performed on an object in which the contained substance is not be able to be viewed from the outside.

In addition, according to the embodiment, an event corresponding to a physical act between objects may be detected if the location relation between those objects satisfies a given condition. Instead of the condition on the location relation between the objects, a condition relating to the recognition of the gesture of a person corresponding to an object may be employed. According to such a configuration, it is possible to realize the constitution of history management described above without requiring any information other than input images. In other words, because there is no need for input information specific to the purpose of an application other than a database to be prepared in advance, it is possible for various persons, such as doctors, nurses, pharmacists, a patient's family, chefs or factory workers to easily accumulate a history or view the accumulated history.

In addition, according to the embodiment, the control content of attributes is determined depending on types defined relating to objects involved in detected events. According to such a configuration, it is possible to distinguish various patterns of actions through combinations of types and realize the control of different attributes for each pattern. Accordingly, it is possible to flexibly apply the constitution of history management described above to various variations of actions, which are targets of history management.

In a situation in which the accuracy of a history is more important, a user interface for receiving an approval on the update of an attribute from a user may be provided. In this case, it is possible to ensure the accuracy of a history to be managed by a slight increase in pressure applied to an operator. In addition, it is possible to verify the time of an action by adding time authenticating data to history data to be stored and increase the reliability and traceability of the history.

Further, a series of control processing by each device described on the disclosure may be realized using any of software, hardware, and a combination of software and hardware. A program composing software is pre-stored in a storage medium installed inside and outside each device, for example. In addition, each program is loaded on a RAM (Random Access Memory) for execution, and is executed by a processor, such as CPU.

In addition, some of the logical functions of each device may be mounted on, instead of that device, a device present in a cloud computing environment. In this case, information communicated between the logical functions can be transmitted or received between devices through the communication unit 112 illustrated in FIG. 2 or the communication unit 212 illustrated in FIG. 5.

Although the preferred embodiments of the present disclosure have been described with reference to the accompanying drawings, a technical scope of the present disclosure is not limited thereto. It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

An information processing device may include an attribute control unit that changes an association between a detected object and an attribute stored in association with the detected object in response to a detected physical action between the detected object and another detected object.

According to one aspect, the device may further include an object identification unit configured to determine the detected physical action via image analysis.

According to another aspect, the device may further include a control unit that changes the association from the attribute that is previously associated with the detected object to being subsequently associated with the another detected object.

According to another aspect, the device may further include an event detection unit that detects the detected physical action as a first event that occurs between the detected object and another detected object, and also detects a second event between the first physical object and a third physical object.

According to another aspect, the first event involves changing the association of the attribute from being stored in association with the detected object to being stored in association with the third physical object.

According to another aspect, the attribute is medicine, and the association of the medicine with a first storage unit is changed to being associated with a second storage unit.

According to another aspect, the event detection unit detects a third event between the first physical object and the third physical object and changes the association of the attribute to be stored in association with the third physical object, and a fourth event between the third physical object and a fourth physical object and further changes the association of the attribute to be stored in association with the fourth physical object, and a fifth event of analyzing a physical feature of the attribute.

According to another aspect, the attribute is a medicine, and the fifth event is a weighing of the medicine.

According to another aspect, the device may further include an event detection unit that detects the detected physical action as a first event that occurs between the detected object and the another detected object, said first detected object being a human, and the second detected object being an object containing medicine, and the detected physical action is the human ingesting the medicine.

According to another aspect, the device may further include an event detection unit that detects the detected physical action as a first event that occurs between the detected object and the another detected object, a second event between the detected object and a third object and associates another attribute with the detected object, a third event of moving the detected object to a fourth object, and According to another aspect, the device may further include a user interface including a display that displays said detected object.

According to another aspect, the device may further include
a data acquisition unit that acquires attribute data, and
an event detection unit that uses the attribute data to determine a characteristic of the detected physical action.

According to another aspect, the device may further include
a display control unit that overlays attribute data adjacent to said detected object on the user interface.

According to another aspect,
said user interface includes a display of at least one of a smartphone, a tablet computer and a head mount display.

According to another aspect,
said event detection unit is configured to detect the first event as at least one of
a distance between two objects being lowering than a predetermined threshold,
a time duration when two objects are located within the predetermined threshold, and
a predetermined gesture.

According to another aspect,
said detected object is one of a source, a transporter and a destination, and said another detected object is one of the source, the transporter and the destination,
said change in association occurs when the source is the detected object and the transporter is the another detected object or when the transporter is the detected object and the destination is the another detected object.

According to another aspect,
the association of the attribute is moved from being stored in association with the detected object to being stored in association with the another detected object.

According to another aspect,
said detected object may also include one of a second transporter, and a scale, and the another detected object may include the second transporter and the scale.

REFERENCE SIGNS LIST 100, 300 Image processing device
120 Image acquisition unit
130 Object identification unit
140 Object DB
142 Object data
144 Attribute control table
150 Event detection unit
160 Attribute DB
162 Attribute data
164 History data
170 Attribute control unit
180 Data distribution unit
190 User interface unit
200 Terminal device
220 Image acquisition unit
230 Data acquisition unit
240 Display control unit
250 User interface unit

The invention claimed is:

1. An information processing device comprising:
at least one processor configured to:
acquire, from an imaging device, first image information including first image data of a first physical object, second image data of a second physical object, and third image data of a third physical object, wherein the first physical object includes a specific physical object and the first image data includes first attribute data associated with the specific physical object;
determine, based on the first image information and via image analysis, whether a first physical action between the first physical object and the second physical object occurs and whether a second physical action between the second physical object and the third physical object occurs, wherein the first physical action is associated with physical contact between at least a part of the specific physical object and the second physical object or between at least a part of the first physical object and the second physical object and the second physical action is associated with physical contact between at least a part of the specific physical object and the third physical object or between at least a part of the second physical object and the third physical object;
add second attribute data to the third image data in accordance with the first physical action and the second physical action, the second attribute data corresponding to the specific physical object; and
send, to an electrical component, the second attribute data when acquiring fourth image data of the third physical object from second image information that is different from the first image information.

2. The information processing device of claim 1, wherein the electrical component includes a user interface including a display configured to display at least one of the first physical object, the second physical object, and the third physical object.

3. The information processing device of claim 2, wherein the at least one processor is configured to control the user interface to display an attribute data image of the second attribute data adjacent to a position corresponding to the third physical object by overlaying the attribute data image over the fourth image data.

4. The information processing device of claim 3, wherein the user interface includes at least one of a smartphone, a tablet computer, and a head mount display.

5. The information processing device of claim 1, wherein the specific physical object is not visible in the fourth image data of the third physical object in the second image information.

6. The information processing device of claim 5, wherein the third physical object is at least one of a container, a human, and a food.

7. The information processing device of claim 6, wherein
the third physical object is the human,
the second attribute data includes at least one of a name of the specific physical object, an ID of the specific physical object, a dosage of the specific physical object, and a feature quantity of the specific physical object, and
the at least one processor is configured to send, to the electrical component, the second attribute data when acquiring image data of the human as the fourth image data.

8. The information processing device of claim 7, wherein
the at least one processor is configured to recognize the human as a patient, and
the specific physical object is at least one of a liquid medicine and a solid medicine.

9. The information processing device of claim 6, wherein the specific physical object is at least one of a liquid medicine, a solid medicine, and a food material.

10. The information processing device of claim 1, wherein the at least one processor is configured to:
acquire third image information including fifth image data of a fourth physical object into which the second physical object is transformed, the third image information being different from each of the first image information and the second image information; and
send, to the electrical component, at least a part of the second attribute data when acquiring the fifth image data of the fourth physical object from the third image information.

11. The information processing device of claim 10, wherein
the fifth image data indicates an appearance image different from that of the third image data, and
the fourth physical object is a food.

12. The information processing device of claim 1, wherein the at least one processor is configured to change the first attribute data when adding the second attribute data to the third image data.

13. The information processing device of claim 12, wherein
the first attribute data includes first supplementary data for a first amount of the specific physical object,
the second attribute data includes second supplementary data for a second amount of the specific physical object, the second amount being associated with the first amount, and
the at least one processor is configured to change the first supplementary data to decrease the first amount when adding the second attribute data to the third image data.

14. The information processing device of claim 12, wherein
the first attribute data is the same as the second attribute data, and
the at least one processor is configured to move the first attribute data from the first image data to the third image data.

15. The information processing device of claim 12, wherein
the first physical action is associated with movement of the specific physical object from the first physical object to the second physical object, and
the second physical action is associated with movement of the specific physical object from the second physical object to the third physical object.

16. The information processing device of claim 1, wherein the at least one processor is configured to send message information in accordance with at least one of the first physical action and the second physical action to a terminal device.

17. The information processing device of claim 16, wherein the at least one processor is configured to send alert information as the message information when at least one of the first physical action and the second physical action is an incorrect action.

18. The information processing device of claim 1, wherein the at least one processor is configured to:
determine that the first physical action occurs in accordance with the first image information when the first physical object approaches the second physical object, and
determine that the second physical action occurs in accordance with the first image information when the second physical object approaches the third physical object.

19. An information processing method comprising:
controlling at least one of a processor of a terminal device, a data server, a network storage, an external memory, and a device present in a cloud computing environment to:
acquire, from an imaging device, first image information including first image data of a first physical object, second image data of a second physical object, and third image data of a third physical object, wherein the first physical object includes a specific physical object and the first image data includes first attribute data associated with the specific physical object;
determine, based on the first image information and via image analysis, whether a first physical action between the first physical object and the second physical object occurs and whether a second physical action between the second physical object and the third physical object occurs, wherein the first physical action is associated with physical contact between at least a part of the specific physical object and the second physical object or between at least a part of the first physical object and the second physical object and the second physical action is associated with physical contact between at least a part of the specific physical object and the third physical object or between at least a part of the second physical object and the third physical object;
add second attribute data to the third image data in accordance with the first physical action and the second physical action, the second attribute data corresponding to the specific physical object; and
send, to an electrical component, the second attribute data when acquiring fourth image data of the third physical object from second image information that is different from the first image information.

20. A non-transitory computer-readable medium storing instructions that, when executed by at least one processor, cause the at least one processor to perform a method comprising:
acquiring, from an imaging device, first image information including first image data of a first physical object, second image data of a second physical object, and third image data of a third physical object, wherein the first physical object includes a specific physical object and the first image data includes first attribute data associated with the specific physical object;
determining, based on the first image information and via image analysis, whether a first physical action between the first physical object and the second physical object occurs and whether a second physical action between the second physical object and the third physical object occurs, wherein the first physical action is associated with physical contact between at least a part of the specific physical object and the second physical object or between at least a part of the first physical object and the second physical object and the second physical action is associated with physical contact between at least a part of the specific physical object and the third physical object or between at least a part of the second physical object and the third physical object;
adding second attribute data to the third image data in accordance with the first physical action and the second physical action, the second attribute data corresponding to the specific physical object; and
sending, to an electrical component, the second attribute data when acquiring fourth image data of the third physical object from second image information that is different from the first image information.

\* \* \* \* \*